United States Patent
Hu et al.

(10) Patent No.: US 9,896,551 B2
(45) Date of Patent: Feb. 20, 2018

(54) PHOSPHAPHENANTHRENE-BASED COMPOUND AND RELATED PREPARATION METHOD AND APPLICATION

(71) Applicant: Elite Electronic Material(Zhongshan) Co., Ltd., Zhongshan, Guangdong Province (CN)

(72) Inventors: Zhi-Long Hu, Zhongshan (CN); Chen-Yu Hsieh, Taoyuan (TW); Xing-Fa Chen, Zhongshan (CN); Xiang Xiong, Zhongshan (CN)

(73) Assignee: Elite Electronic Material(Zhongshan) Co., Ltd., Zhongshan, Guangdong Province (CN)

( * ) Notice: Subject to any disclaimer, the term of this patent is extended or adjusted under 35 U.S.C. 154(b) by 0 days.

(21) Appl. No.: 15/086,047

(22) Filed: Mar. 30, 2016

(65) Prior Publication Data
US 2017/0022228 A1 Jan. 26, 2017

(30) Foreign Application Priority Data

Jul. 24, 2015 (CN) .......................... 2015 1 0443938

(51) Int. Cl.
*C08G 79/04* (2006.01)
*C07F 9/6571* (2006.01)

(52) U.S. Cl.
CPC ........ *C08G 79/04* (2013.01); *C07F 9/657172* (2013.01)

(58) Field of Classification Search
CPC .......................... C08G 79/04; C07F 9/657172
USPC ........................................................ 523/435
See application file for complete search history.

(56) References Cited

U.S. PATENT DOCUMENTS

2014/0039108 A1* 2/2014 Kurokawa ............... C08K 3/22
524/377

FOREIGN PATENT DOCUMENTS

JP 2001270993 A * 10/2001 ............ C08L 101/00

OTHER PUBLICATIONS

Koyama et all., JP 2001-270993 A machine translation in English, Oct. 2, 2001.*

* cited by examiner

*Primary Examiner* — David T Karst
(74) *Attorney, Agent, or Firm* — Winston Hsu

(57) ABSTRACT

Provided is a phosphaphenanthrene-based compound represented by the following chemical structure:

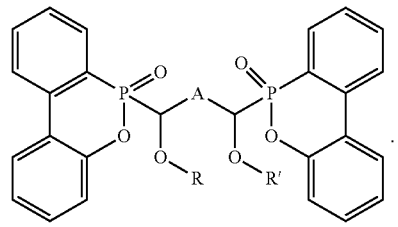

The phosphaphenanthrene-based compound can be added in a resin composition and made into a prepreg or resin film. The prepreg or resin film made from such resin composition has low coefficient of thermal expansion, low dielectric constant and dissipation factor, and flame retardancy, thereby being suitable for copper-clad laminate or printed circuit board.

15 Claims, 6 Drawing Sheets

PHOSPHAPHENANTHRENE-BASED COMPOUND AND RELATED PREPARATION METHOD AND APPLICATION

BACKGROUND OF THE INVENTION

1. Field of the Invention

The present invention relates to a preparation method of a phosphaphenanthrene-based compound, and more particularly, to a phosphaphenanthrene-based compound applicable to copper-clad laminates (CCL) and printed circuit boards and related preparation method.

2. Description of the Prior Art

Printed circuit boards are widely used in various applications, such as large-scale industrial computers, communication devices, electrical measurements, national defense and aviation products, and consumer electronic products. As technology advances, various electronic products are designed to be miniaturized and multi-functional and have high performance and high reliability. Accordingly, the design and development of printed circuit boards tend to high precision, high density, and high performance and to be micro-porous, thinned and multi-layered.

A reflow process (such as IR-reflow) is required for mounting the surface components (such as active components or passive components) on the printed circuit boards, such that the lead-free solders are melted to connect the surface components with the metal lines on the printed circuit boards. Generally, the resin material constituted the insulating layer of the printed circuit boards is easily deformed after suffering heat impact of the reflow process due to different coefficients of thermal expansion. Accordingly, the laminate is warped and deformed and the flatness of the laminate is decreased, thereby problems of poor welding (e.g., nonwetting or false soldering) occur. Since the calorific power increases as the density of the interconnection of the printed circuit board becomes higher, to reduce the coefficient of thermal expansion of the insulating layer is an important topic to be addressed and discussed.

Take the epoxy resin composition as an example for the material of the printed circuit boards, various flame retardants (e.g., halogen flame retardants and phosphorus-containing flame retardants) have been used to provide a suitable flame retardancy for the material. Among them, the halogen flame retardants are forbidden due to environmental issues, while the applications of the phosphorus-containing flame retardants, e.g., phosphate ester (Taiwan Patent No. I238846) and red phosphorus (Taiwan Patent No. 322507) are limited. The reason is that the hydrolysis reaction of the phosphate ester would generate acid which affects the migration resistance of the phosphate ester, and small quantities of phosphine gas would be produced when the red phosphorus is in a hot and humid environment, thereby the red phosphorus is considered dangerous. Accordingly, the application of the above two kinds of phosphorus-containing flame retardants are limited.

In addition, the conventional phosphazene compound (e.g., SPB-100 produced by Otsuka Chemical) has no functional groups, and therefore the conventional phosphazene compound added to the halogen-free resin composition may not be able to react and bond with other resins. Furthermore, the melting point of the condensed phosphate ester (PX-200) is low and the migration of the condensed phosphate ester is too high at high temperature. Accordingly, the coefficient of thermal expansion of the laminate manufactured from the resin composition is large such that inner cracking are caused during the manufacturing process of the circuit boards and the process yield is reduced.

Consequently, the phosphaphenanthrene-based compound and its derivatives become important due to their molecular structure containing phosphorus atom, biphenyl ring, and phenanthrene ring. Among them, though the hydroxyl group in 2-(10H-9-oxa-10-phospha-1-phenanthryl)hydroquinone phosphorus oxide (DOPO-HQ) may react and bond with other resins, the hydroxyl group would have negative impact on the dielectric constant and the dissipation factor, wherein the dielectric constant of the copper-free laminate (the resin content is about 55%) measured at 10 GHz is higher than 4.0 and the dissipation factor of the copper-free laminate at 10 GHz is higher than 0.010. Accordingly, it is still not suitable to add the phosphaphenanthrene-based compound having the hydroxyl group into the resin composition since it's difficult for the resin composition with the phosphaphenanthrene-based compound to have low dielectric property.

SUMMARY OF THE INVENTION

In view of the above-mentioned technical drawbacks, one of the objectives of the present invention is to provide a phosphaphenanthrene-based compound which can be applied to a resin composition for manufacturing a prepreg or a resin film to thereby be further applicable to copper-clad laminates and printed circuit boards, such that the copper-clad laminates and printed circuit boards can have satisfactory properties, namely low coefficient of thermal expansion, low dielectric property, high heat resistant, and good flame retardancy.

To achieve the above objective, the present invention provides a phosphaphenanthrene-based compound being of a structure expressed by formula (I) below:

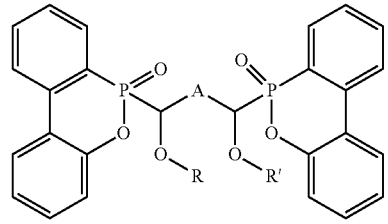

Formula (I)

Wherein R and R' are each independently a hydrogen (H) atom, a vinyl-substituted alkyl group with 3 to 20 carbon atoms, a vinyl-substituted cycloalkyl group with 8 to 20 carbon atoms, a vinyl-substituted benzyl group with 9 to 20 carbon atoms, or a vinyl-substituted aromatic functional group with 8 to 20 carbon atoms; and
A is a covalent bond, an arene-diyl group with 6 to 20 carbon atoms, a cycloalkane-diyl group with 3 to 12 carbon atoms, a cycloalkene-diyl group with 6 to 12 carbon atoms, a methylene group (—CH$_2$—), or an alkane-diyl group with 2 to 12 carbon atoms.

The arene-diyl group with 6 to 20 carbon atoms may be

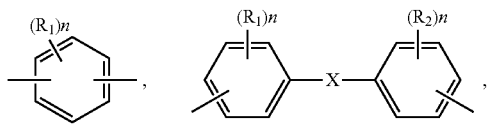

-continued

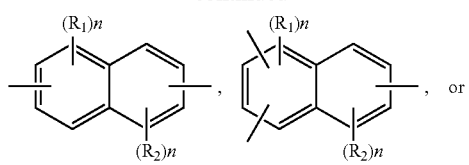

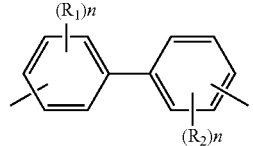

for example;

wherein $R_1$ and $R_2$ are each independently an alkyl group with 1 to 3 carbon atoms, X is —$CH_2$—,

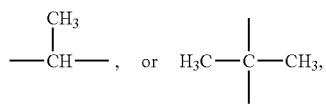

and n is an integer ranging from 0 to 4.

For example, the vinyl-substituted alkyl group with 3 to 20 carbon atoms may be 1-propenyl group (—CH=CHCH$_3$), 1-isopropenyl group (—C(CH$_3$)=CH$_2$), 2-propenyl group (—CH$_2$CH=CH$_2$), 2-butenyl group (—CH$_2$CH=CHCH$_3$), or 3-butenyl group (—CH$_2$CH$_2$CH=CH$_2$), but not limited thereto; and the vinyl-substituted cycloalkyl group with 8 to 20 carbon atoms may be 4-vinyl cyclohexyl group

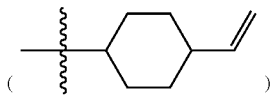 [SMILES: *C1CCC(C=C)CC1]

or 2-vinyl cyclohexyl group

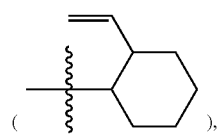

but not limited thereto; the vinyl-substituted benzyl group with 9 to 20 carbon atoms may be 4-vinyl benzyl group

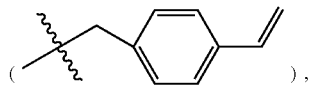

but not limited thereto; the vinyl-substituted aromatic functional group with 8 to 20 carbon atoms may be 4-vinyl phenyl group

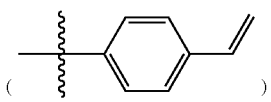 [SMILES: *c1ccc(C=C)cc1]

or 4-vinyl naphthalenyl group

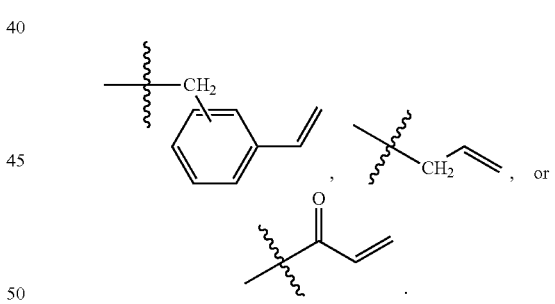

but not limited thereto.

Preferably, R and R' are each independently a vinyl- and carbonyl-substituted alkyl group with 3 to 20 carbon atoms, a vinyl- and carbonyl-substituted cycloalkyl group with 8 to 20 carbon atoms, a vinyl- and carbonyl-substituted benzyl group with 9 to 20 carbon atoms or a vinyl- and carbonyl-substituted aromatic group with 8 to 20 carbon atoms. Alternatively, R and R' are each independently a vinyl-substituted alkyl group with 3 to 20 carbon atoms that is unsubstituted with carbonyl group, a vinyl-substituted cycloalkyl group with 8 to 20 carbon atoms that is unsubstituted with carbonyl group, a vinyl-substituted benzyl group with 9 to 20 carbon atoms that is unsubstituted with carbonyl group, or a vinyl-substituted aromatic group with 8 to 20 carbon atoms that is unsubstituted with carbonyl group.

Preferably, R and R' are each independently

Accordingly, the phosphaphenanthrene-based compound may have a better solubility in solvents.

Preferably, R and R' may be the same or different substituents. More preferably, when R and R' are hydrogen at the same time, A is not

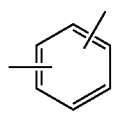

Preferably, the phosphaphenanthrene-based compound may have a structure expressed below:

Formula (II)

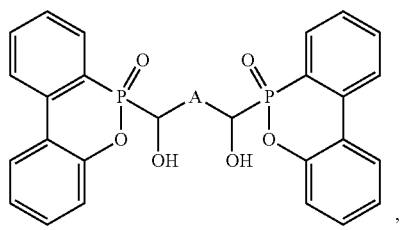

Wherein A is

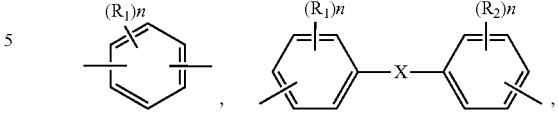

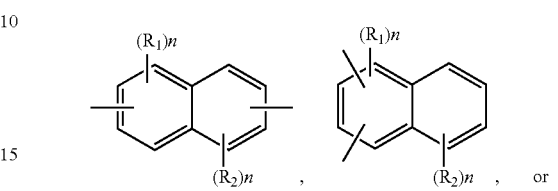

Formula (III)

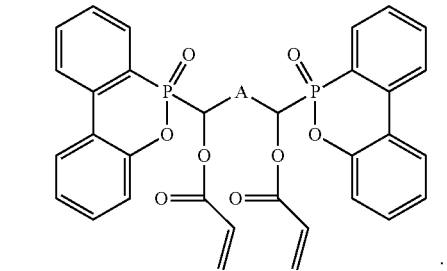

wherein $R_1$ and $R_2$ are each independently an alkyl group with 1 to 3 carbon atoms, X is —$CH_2$—,

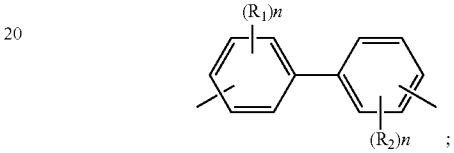

and n is an integer ranging from 0 to 4.

Specifically, if n is 0, the carbon atoms in one of the above-mentioned aromatic functional group representing A is bonded with only one hydrogen atom, without being bonded with an alkyl group.

Preferably, when n is an integer between 2 to 4, $R_1$ may be the same or different foregoing substituent groups, and $R_2$ may also be the same or different foregoing substituent groups.

More specifically, the phosphaphenanthrene-based compound may have a structure expressed below:

Formula (IV)

Formula (V)

or

Formula (VI)

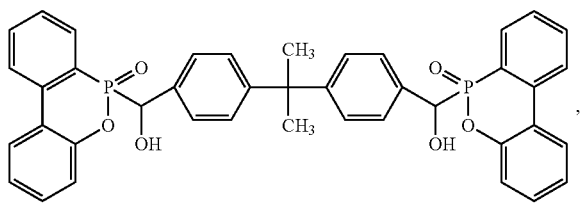

Formula (VII)

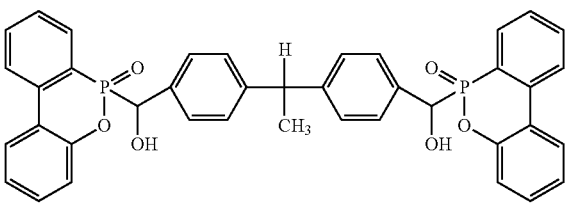

-continued
Formula (VIII)
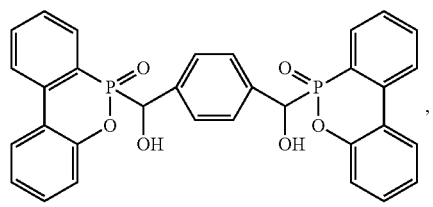
Formula (IX)
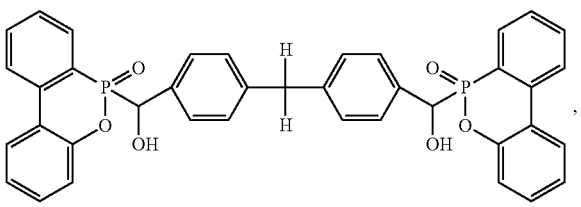
Formula (X)
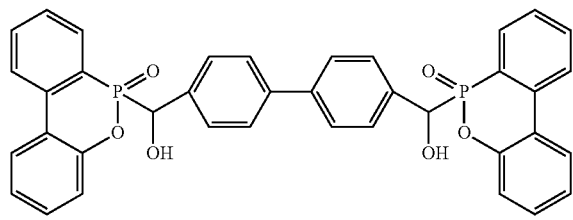
Formula (XI)
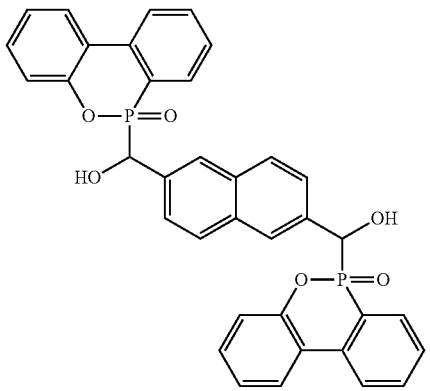
Formula (XII)
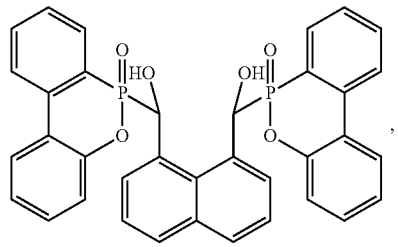
Formula (XIII)
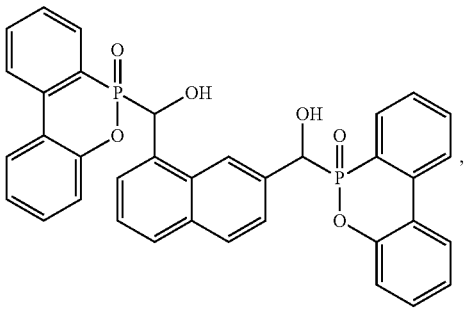
Formula (XIV)
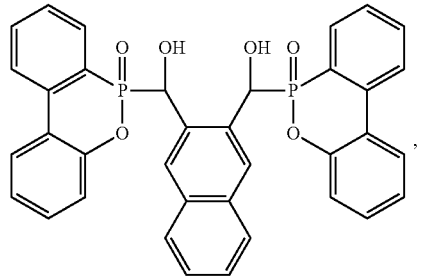
Formula (XV)
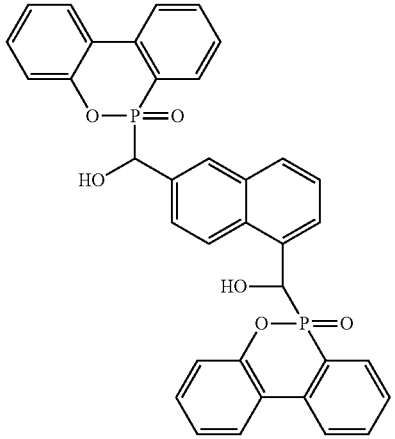

-continued
Formula (XVI)
Formula (XVII)
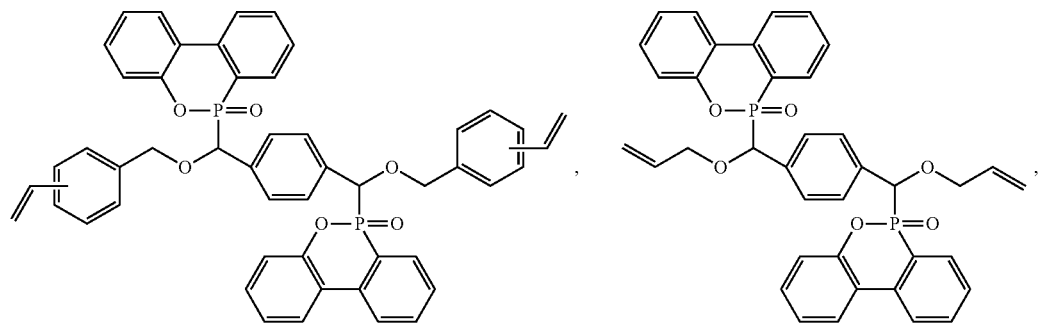
Formula (XVIII)
Formula (XIX)
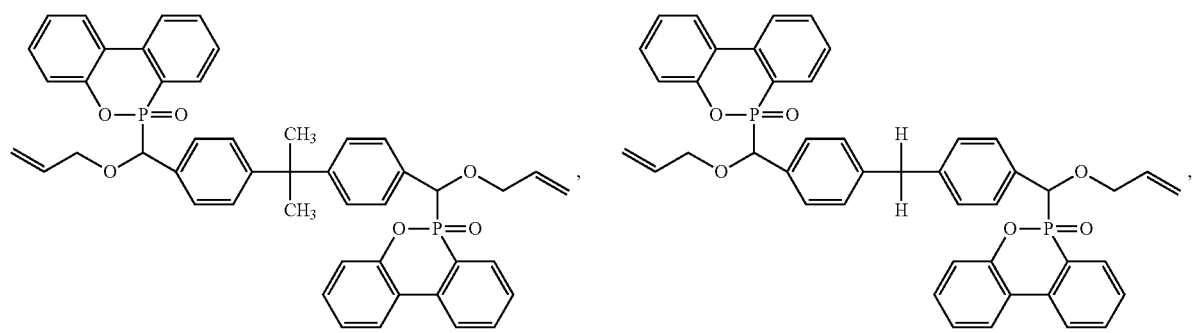
Formula (XX)
Formula (XXI)
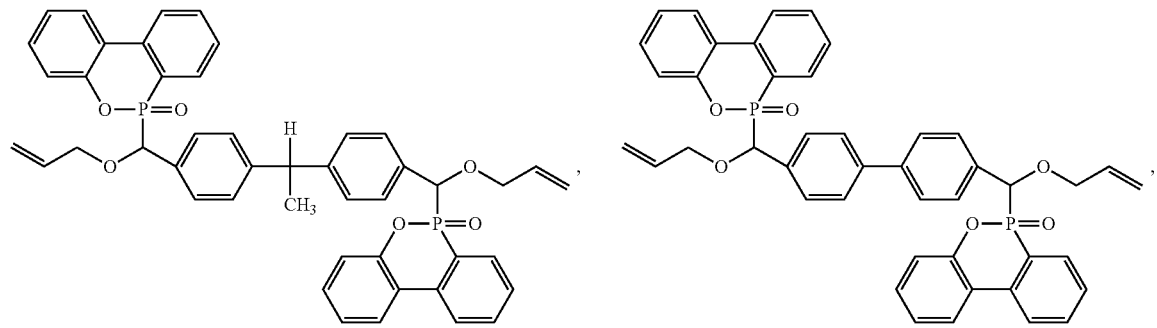
Formula (XXII)
Formula (XXIII)
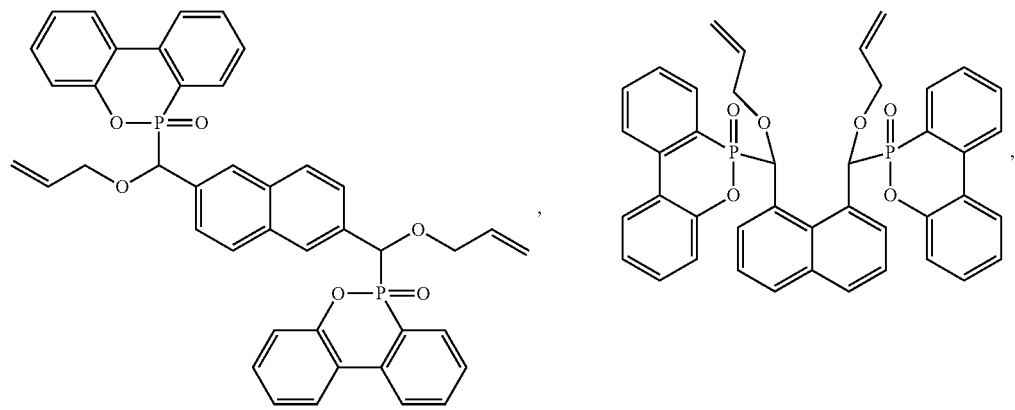

Formula (XXIV)
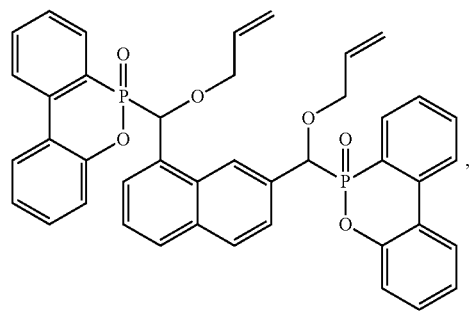
Formula (XXV)
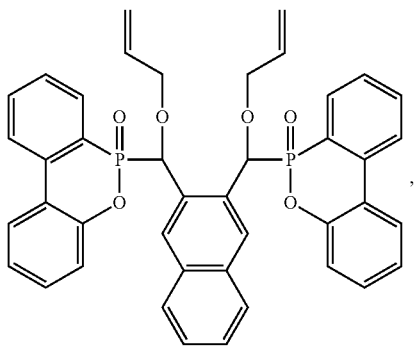
Formula (XXVI)
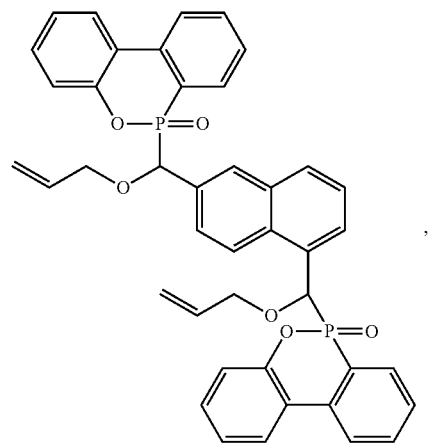
Formula (XXVII)
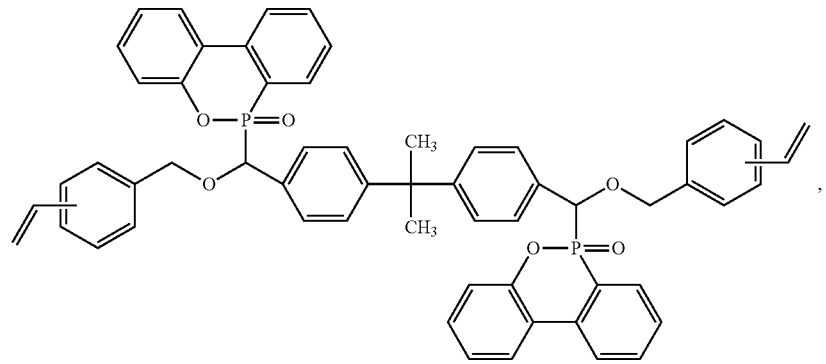
Formula (XXVIII)
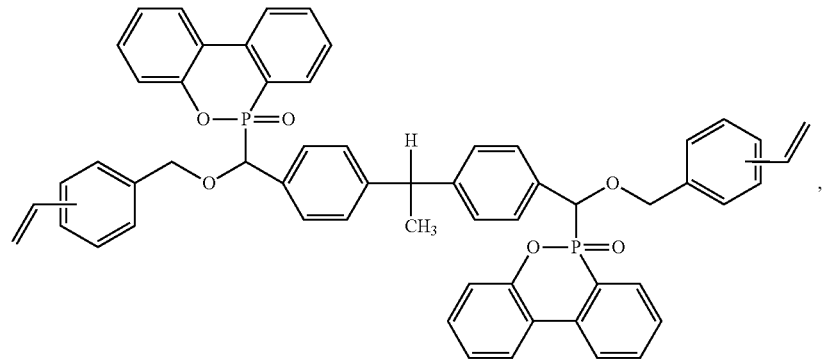

-continued
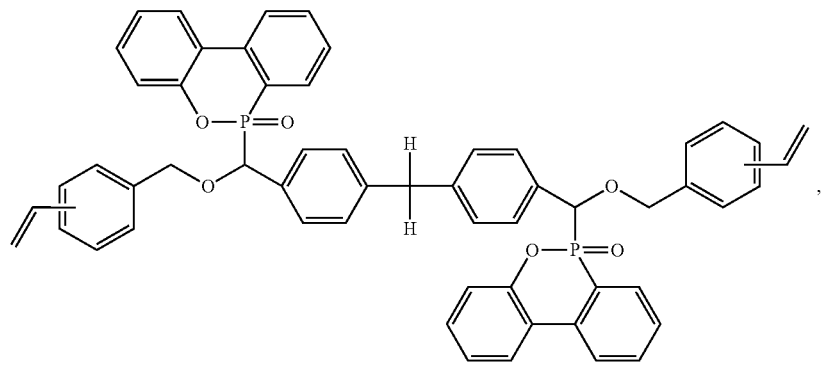
Formula XXIX)
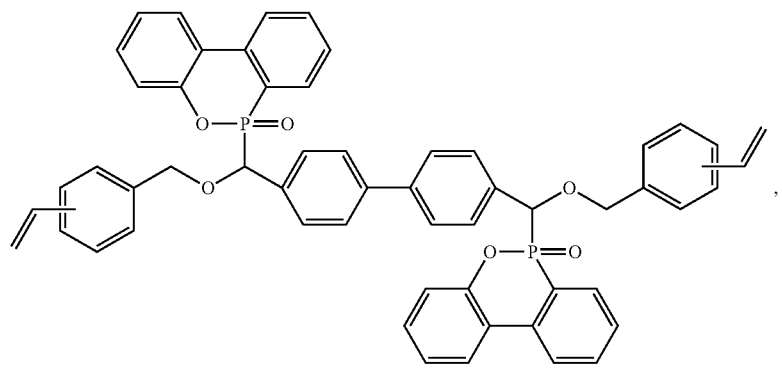
Formula (XXX)
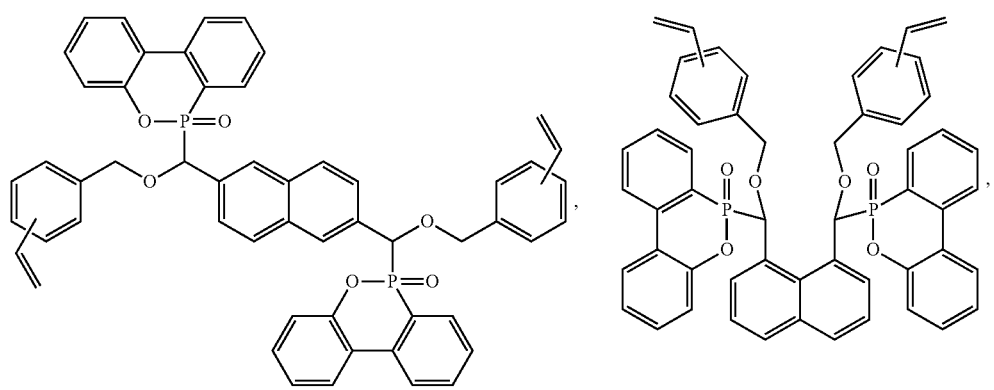
Formula (XXXI)  Formula (XXXII)
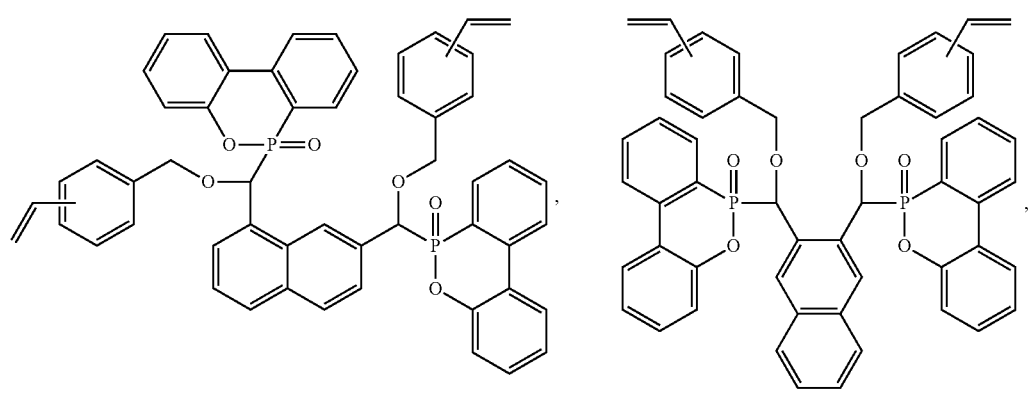
Formula (XXXIII)  Formula (XXXIV)

-continued

Formula (XXXV)

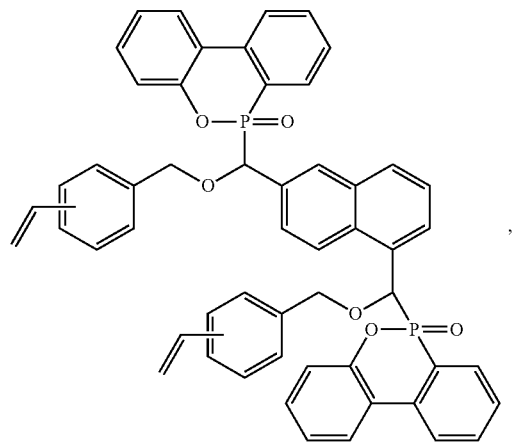

Formula (XXXVI)

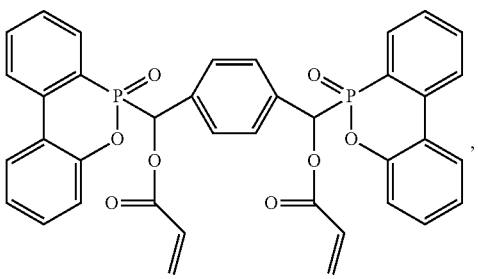

The present invention further provides a preparation method of a phosphaphenanthrene-based compound. The preparation method includes reacting 9,10-dihydro-9-oxa-10-phosphaphenanthrene-10-oxide (DOPO) with a dialdehyde compound to form the phosphaphenanthrene-based compound having a structure expressed by formula (II) above. In other words, the phosphaphenanthrene-based compound prepared by the foregoing method is a phosphaphenanthrene-based compound having hydroxyl group. Wherein A is

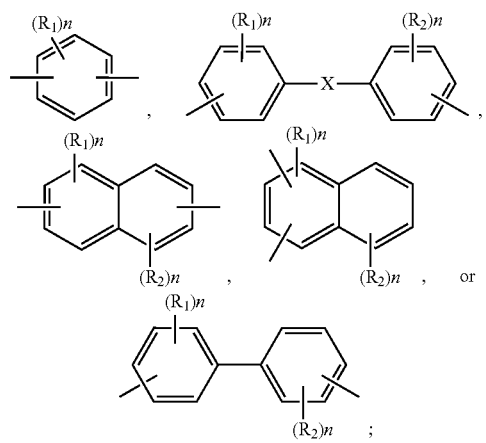

$R_1$ and $R_2$ are each independently an alkyl group with 1 to 3 carbon atoms; X is —$CH_2$—,

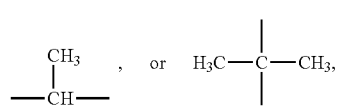

and n is an integer ranging from 0 to 4.

More specifically, the aforementioned preparation method includes providing a heating reflux environment to react the DOPO with the dialdehyde compound in a solvent, wherein the reflux time may range from 1 to 7 hours, and the reaction temperature may range from 50° C. to 200 t.

Preferably, the solvent is toluene (TL), dimethylacetamide (DMAC), dimethylformamide (DMF), 2-propanol methyl ether (PM), propylene glycol methyl ether acetate (PMA), cyclohexanone (CYC), acetone or methyl ethyl ketone (MEK).

Preferably, the dialdehyde compound is a dialdehyde compound having aromatic functional group (s). More preferably, the dialdehyde compound is at least one selected from the group consisting of the following: 1,4-phthalaldehyde, 1,3-phthalaldehyde, 1,2-phthalaldehyde, 2,3-naphthalenedicarboxaldehyde, 1,6-naphthalenedicarboxaldehyde, 1,8-naphthalenedicarboxaldehyde, 1,7-naphthalenedicarboxaldehyde, 4,4'-biphenyldicarboxaldehyde, 4,4'-xenygloxal, bisphenol A based dialdehyde, bisphenol F based dialdehyde, and bisphenol E based dialdehyde.

The present invention further provides a preparation method of phosphaphenanthrene-based compound, including: reacting DOPO with a dialdehyde compound to form a phosphaphenanthrene-based compound having hydroxyl group; and reacting the phosphaphenanthrene-based compound having hydroxyl group with a vinyl-based compound to form the phosphaphenanthrene-based compound which has a structure expressed by formula (I) above.

Wherein R and R' are each independently a vinyl-substituted alkyl group with 3 to 20 carbon atoms, a vinyl-substituted cycloalkyl group with 8 to 20 carbon atoms, a vinyl-substituted benzyl group with 9 to 20 carbon atoms, or a vinyl-substituted aromatic group with 8 to 20 carbon atoms; and A is

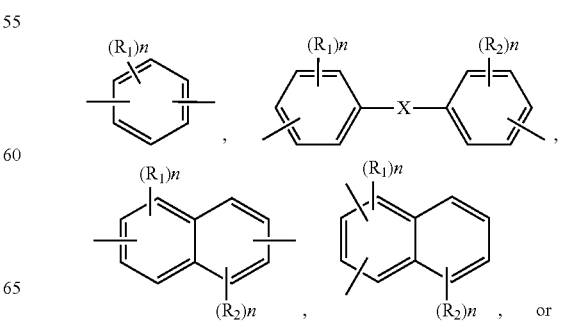

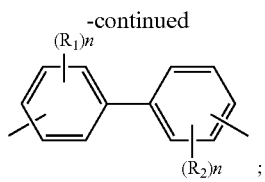

wherein $R_1$ and $R_2$ are each independently an alkyl group with 1 to 3 carbon atoms; X is —$CH_2$—,

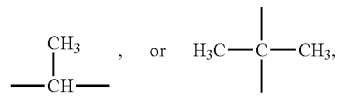

and n is an integer ranging from 0 to 4.

In other words, the phosphaphenanthrene-based compound prepared by the foregoing method is a vinyl-containing phosphaphenanthrene-based compound.

Accordingly, with the introduction of vinyl, the melting point of the aforementioned vinyl-containing phosphaphenanthrene-based compound may be greater than about 250° C. Thus, compared to a known commercially available phosphorus-containing curing agent, the vinyl-containing phosphaphenanthrene-based compound of the present invention has both higher melting point and better solubility compatibility. Consequently, the vinyl-containing phosphaphenanthrene-based compound of the present invention may be better dispersed in the resin composition. As such, the prepreg and copper-clad laminate manufactured by the resin composition having vinyl-containing phosphaphenanthrene-based compound of the present invention may have better dielectric property and lower coefficient of thermal expansion.

The vinyl compound is a compound containing carbon-carbon double bond(s). Preferably, the vinyl compound is selected from the group consisting of the following: 4-chloromethyl styrene, 3-chlro-methyl styrene, 2-chlro-methyl styrene, allyl chloride, acrylic acid, and acryloyl chloride.

Preferably, the step of reacting the phosphaphenanthrene-based compound having hydroxyl group with the vinyl compound to form the phosphaphenanthrene-based compound includes carrying out a reaction of the phosphaphenanthrene-based compound having hydroxyl group and the vinyl compound in the solvent of toluene in the presence of hydroxide and tetrabutylammonium halide so as to form the vinyl-containing phosphaphenanthrene-based compound. More preferably, the reaction temperature of the aforementioned reaction may range from 50° C. to 70° C., and the reaction time may range from 6 to 10 hours.

More preferably, an addition amount of the phosphaphenanthrene-based compound having hydroxyl group is 1 mole, an addition amount of the vinyl compound ranges from 2 moles to 4 moles, an addition amount of the hydroxide ranges from 2 moles to 4 moles, and an addition amount of the tetrabutylammonium halide ranges from 0.1 moles to 0.3 moles. Even more preferably, the addition amount of the vinyl compound ranges from 2.2 moles to 3 moles, the addition amount of the hydroxide ranges from 2.2 moles to 3 moles, and an addition amount of the tetrabutylammonium halide ranges from 0.15 moles to 0.2 moles.

Preferably, the aforementioned vinyl compound is styrene compound; the aforementioned hydroxide may be sodium hydroxide or potassium hydroxide; and the aforementioned tetrabutylammonium halide may be tetrabutylammonium bromide or tetrabutylammonium iodide.

Preferably, the purity of the obtained phosphaphenanthrene-based compound may be elevated through further washing the initial product with methanol to remove the byproducts and impurities after the reaction. Wherein, the byproducts and impurities refer to sodium halide (e.g., sodium chloride) produced from the halogen-containing reactant after the reaction.

In the preparation methods of the above-described two kinds of phosphaphenanthrene-based compounds, preferably, the mole ratio of the DOPO and the dialdehyde compound ranges from 2:1 to 4:1, and more preferably, the mole ratio of the DOPO and the dialdehyde compound ranges from 2:1 to 3:1.

The present invention further provides a resin composition containing the above-mentioned phosphaphenanthrene-based compound(s), and the resin composition includes the above-mentioned phosphaphenanthrene-based compound(s) and reactant(s).

Accordingly, compared to other known commercially available phosphorus-containing flame retardants, when the resin composition manufactured by mixing the phosphaphenanthrene-based compound of the present invention with the reactant(s) is applied to the printed circuit board, the printed circuit board is halogen-free and capable of having better flame resistance, lower Z-axis expansion coefficient, lower dielectric property, better heat resistance, and better flame retardancy.

Preferably, an amount of the reactant(s) is 100 parts by weight, and an amount of the phosphaphenanthrene-based compound ranges from 5 parts by weight to 80 parts by weight. More preferably, if the amount of the reactant(s) is 100 parts by weight, the amount of the phosphaphenanthrene-based compound ranges from 5 parts by weight to 60 parts by weight. More preferably, if the amount of the reactant is 100 parts by weight, the amount of the phosphaphenanthrene-based compound ranges from 7.1 parts by weight to 50 parts by weight.

Preferably, the reactant(s) includes any one of epoxy resin, phenol resin, isocyanurate resin, cyanate ester resin, benzoxazine resin, styrene-maleic anhydride, polyester, maleimide, polyphenylene ether resin, amine curing agent, phenoxy resin, styrene, polyamide, polyimide, and polyolefin, or a combination thereof.

Preferably, the resin composition further includes an additive, and the additive includes at least one component selected from a group consisting of a curing accelerator, a flame retardant, an inorganic filler, a solvent, a toughing agent, and a silane coupling agent. If the amount of the reactants is 100 parts by weight, the amount of the additive ranges from 0.01 parts by weight to 500 parts by weight. More preferably, if the amount of the reactant(s) is 100 parts by weight, the amount of the curing accelerator ranges from 0.01 parts by weight to 10 parts by weight.

The epoxy resin applied to the present invention is not particularly limited, and any resin having epoxy functional group or modified epoxy resin thereof are suitable. Specifically, the suitable epoxy resin includes at least one selected from a group consisting of bisphenol A epoxy resin, bisphenol F epoxy resin, bisphenol S epoxy resin, bisphenol AD epoxy resin, phenol novolac epoxy resin, bisphenol A novolac epoxy resin, bisphenol F novolac epoxy resin, o-cresol novolac epoxy resin, trifunctional epoxy resin, tetrafunctional epoxy resin, multifunctional epoxy resin, dicyclopentadiene (DCPD) epoxy resin, phosphorus-containing epoxy resin, DOPO epoxy resin, DOPO-HQ epoxy resin, p-xylene epoxy resin, naphthalene epoxy resin, benzopyran epoxy resin, biphenyl novolac epoxy resin, isocyanate modified epoxy resin, phenol benzaldehyde epoxy resin and phenol aralkyl novolac epoxy resin. The aforementioned DOPO epoxy resin may be DOPO containing-phenol novolac (DOPO-PN) epoxy resin, DOPO containing-cresol novolac (DOPO-CN) epoxy resin, or DOPO containing-bisphenol novolac (DOPO-BPN) epoxy resin, such as DOPO-bisphenol A novolac epoxy resin and DOPO-bisphenol F novolac epoxy resin. The aforementioned DOPO epoxy resin may also be DOPO-HQ containing-PN epoxy resin, DOPO-HQ-CN epoxy resin, or DOPO-HQ-BPN epoxy resin.

The phenol resin suitable for the present invention may be monofunctional phenol resin, difunctional phenol resin or multifunctional phenol resin. The above-described phenol resin is not particularly limited, and the phenol resins used in the industry at present are all within the scope of the phenol resin suitable for the present invention.

The cyanate ester resin of the present invention is not particularly limited, and the known commercially available cyanate ester resins are all suitable, which have the structure of Ar—O—C≡N. Wherein, Ar may be a substituted or unsubstituted aromatic functional group, e.g., novolac based cyanate ester resin, bisphenol A based cyanate ester resin, bisphenol A novolac cyanate ester resin, bisphenol F based cyanate ester resin, bisphenol F novolac cyanate ester resin, cyanate ester resin having dicyclopentadiene structure, cyanate ester resin having naphthalene ring structure and phenolphthalein based cyanate ester resin. Examples of cyanate ester resin are, but not limited to, cyanate ester resins with tradenames Primaset PT-15, PT-30S, PT-60S, CT-90, BADCY, BA-100-10T, BA-200, BA-230S, BA-300S, BTP-2500, BTP-6020S, DT-4000, DT-7000, Methylcy, ME-240S, etc., produced by Lonza. The cyanate ester resins mentioned above may be added to the resin composition of the present invention independently or in a combination form.

The polyester resin suitable for the present invention may be formed through the esterification reaction between an aromatic having a dicarboxylic acid group and an aromatic having a dihydroxyl group, such as the HPC-8000T65 commercially available from Dainippon Ink & Chemicals.

The benzoxazine resin suitable for the present invention may be bisphenol A based benzoxazine resin, bisphenol F based benzoxazine resin, phenolphthalein based benzoxazine resin, dicyclopentadiene benzoxazine resin, or phosphorus-containing benzoxazine resin, e.g., LZ-8270 (phenolphthalein based benzoxazine resin), LZ-8280 (bisphenol F based benzoxazine resin), or LZ-8290 (bisphenol A based benzoxazine resin) produced by Huntsman or HFB-2006 M produced by Showa Polymer Company.

The amine curing agent for the present invention may be dicyandiamide, diaminodiphenyl sulfone, diaminodiphenyl methane, diaminodiphenyl ether, diaminodiphenyl sulfide, or a combination thereof.

The polyolefin suitable for the present invention may be a styrene-butadiene-divinylbenzene terpolymer, a styrene-butadiene-maleic anhydride terpolymer, a vinyl-polybutadiene-urethane oligomer, polybutadiene, a styrene-butadiene copolymer, a hydrogenated styrene-butadiene copolymer, a styrene-isoprene copolymer, a hydrogenated styrene-isoprene copolymer, a methylstyrene copolymer, a petroleum resin, a cyclic olefin copolymer or a combination thereof.

The ratio of styrene (S) and maleic anhydride (MA) of the styrene-maleic anhydride resin of the present invention may be 1:1, 2:1, 3:1, 4:1, 6:1 or 8:1, such as the styrene-maleic anhydride copolymer product of SMA-1000, SMA-2000, SMA-3000, EF-30, EF-40, EF-60 and EF-80 commercially available from Cray Valley, but not limited thereto. Further, the styrene-maleic anhydride resin may be esterified styrene-maleic anhydride copolymers, such as the product esterified styrene-maleic anhydride copolymer product of SMA1440, SMA17352, SMA2625, SMA3840 and SMA31890 commercially available from Cray Valley. The aforementioned styrene-maleic anhydride resin may be added to the resin composition of the present invention independently or in a combination form.

The polyphenylene ether resin suitable for the present invention may be a polyphenylene ether resin with terminal hydroxyl group (e.g., SA-90, commercially available from Sabic), a bisphenol A polyphenylene ether resin with methacrylate terminal group (e.g., SA-9000, commercially available from Sabic), a diphenyl polyphenylene ether resin with terminal vinylbenzyl group (e.g., OPE-2st, commercially available from Mitsubishi Gas Chemical).

The maleimide suitable for the present invention may be 4,4'-diphenyl methane bismaleimide, phenyl methane maleimide oligomer, N,N'-m-phenylenebismaleimide, bisphenol A diphenyl ether bismaleimide, 3,3'-dimethyl-5,5'-diethyl-4,4'-diphenylmethane bismaleimide, N,N'-(4-methyl-1,3-phenylene) bismaleimide, 1,6-bismaleimide-(2,2,4-trimethyl)hexane, N-2,3-xylylmaleimide, N-2,6-xylenemaleimide, N-phenylmaleimide or a prepolymer thereof. For example, the prepolymer may be a prepolymer of diallyl compound and maleimide.

One or more curing accelerators may be optionally added into the resin composition of the present invention in order to improve the curing rate of the resin composition. Any curing accelerator that accelerates the curing rate of the resin composition of the present invention may be used. The curing accelerator may include a Lewis base catalyst or a Lewis acid catalyst. The Lewis base catalyst includes at least one of imidazole, a boron trifluoride-amine complex, ethyltriphenylphosphonium chloride, 2-methylimidazole, 2-phenyl imidazole, 2-ethyl-4-methylimidazole, triphenylphosphine and 4-dimethyl amino pyridine. The Lewis acid includes metal salt compound. For example, the metal salt compound may be at least one of the salts of manganese, iron, cobalt, nickel, copper and zinc. Preferably, the Lewis acid is a metal catalyst, such as zinc octoate, cobalt octoate, cobalt acetylacetone and zinc acetylacetone. Alternatively, the curing accelerator may also include generating peroxide capable of generating free radical, for example, including but not limited to: dicumyl peroxide, t-butyl peroxybenzoate, 2,5-dimethyl-2,5-di(t-butylperoxy)-3-hexyne, bis(tert-butylperoxy isopropyl) benzene, or a combination thereof.

Preferably, if an amount of the reactant is 100 parts by weight, an inorganic filler with 10 to 200 parts by weight may be further added into the resin composition of the present invention in order to increase the thermal conductivity, thermal expansion and mechanical strength of the resin composition, and the added inorganic filler may be uniformly distributed in the resin composition.

The inorganic filler suitable for the present invention includes one or more of silica (with fused state, non-fused state, porous type or hollow type), alumina, aluminum hydroxide, magnesia, magnesium hydroxide, calcium carbonate, aluminum nitride, boron nitride, aluminum silicon carbide, silicon carbide, sodium carbonate, titanium dioxide, zinc oxide, zirconia, quartz, diamond powder, diamond-like powder, graphite, magnesium carbonate, potassium titanate, ceramic fibers, mica, boehmite (AlOOH), zinc molybdate, ammonium molybdate, zinc borate, calcium phosphate, calcination talc, talc, silicon nitride, mullite, calcination kaolin, clay, basic magnesium sulfate whisker, mullite whisker, barium sulfate, magnesium hydroxide whisker, magnesium oxide whisker, calcium oxide whisker, carbon nanotubes, nano-grade silicon dioxide and related inorganic powders or powder particles having an organic core outer shell as an insulator modification. The inorganic filler may be spherical, fibrous, plate-shaped, granular, sheet-shaped or whisker, and may be optionally pretreated with a silane coupling agent.

The present invention provides a resin product which is formed by curing the aforementioned resin composition. Specifically, the resin product may be a prepreg, a resin film, a copper-clad laminate or a printed circuit board.

Specifically, the present invention provides a prepreg having a reinforcing material and a layered material disposed on the reinforcing material, wherein the layered material was made by semi-curing the resin composition. By using the aforementioned resin composition, the prepreg of the present invention features a low coefficient of thermal expansion, a low dielectric constant, a low dissipation factor, a high heat resistance, a high flame resistance, and halogen-free. Wherein, the resin composition is attached to the reinforcing material through impregnation and heated up at a high temperature to become semi-cured (i.e. cured to B-staged), so as to form the prepreg.

The reinforcing material suitable for the present invention includes a fibrous material, a woven fabric or a non-woven fabric, such as a glass fiber fabric, so as to increase the mechanical strength of the prepreg. Preferably, the reinforcing material may be optionally pretreated with a silane coupling agent.

The aforementioned prepreg may be cured to forma fully-cured (i.e. C-staged) prepreg or a cured-state insulating layer through being heated at a high temperature or at a high temperature and a high pressure. If the resin composition includes a solvent, the solvent will evaporate and escape during the high-temperature heating process.

The present invention further provides a resin film which is made from the cured resin composition that suffers heat baking. The resin composition may be selectively coated to a polyethylene terephthalate film (PET film), a polyimide film or a resin coated copper (RCC), followed by heat baking to be semi-cured and form a resin film. Accordingly, the laminate features a low coefficient of thermal expansion, a low dielectric constant, a low dissipation factor, a high heat resistance, a flame resistance, and halogen-free.

The present invention further provides a laminate including two metal foils and one insulating layer superimposed between the metal foils. The insulating layer may be formed by curing the aforementioned prepreg or resin film under high temperature and high pressure through superimposed the aforementioned prepreg or resin film between the metal foils. The material of the metal foils may be copper, aluminum, nickel, platinum, silver, gold or an alloy of any of the above-mentioned material. The laminates may be, for example, a copper-clad laminate (CCL).

By using the aforementioned resin composition, the laminate has advantages such as low coefficient of thermal expansion, low dielectric constant, low dissipation factor, good heat resistance, good flame resistance and being halogen-free, and is particularly suitable for high speed and high frequency signal transmission printed circuit board. The laminate may be further processed to form printed circuit board whose quality will not be affected when it is jointed with electronic elements and operated at high temperature, high humidity and other harsh environment.

Compared to conventional technology, the phosphaphenanthrene-based compound of the present invention has a better flame retardancy. In addition, the phosphaphenanthrene-based compound having hydroxyl group has a high melting point, and the migration of DOPO at high temperature is small, so that the laminate made from the resin composition has properties of low coefficient of thermal expansion, low dielectric constant, and low dissipation factor. Furthermore, the vinyl-containing phosphaphenanthrene-based compound includes less polarity reactive functional group and has good solubility, so that the laminate made from the resin composition has lower coefficient of thermal expansion, lower dielectric constant, and lower dissipation factor, and the appearance of the prepreg is smooth and flat.

In summary, the phosphaphenanthrene-based compound of the present invention has the following advantages:

1. The phosphaphenanthrene-based compound of the present invention has the reactive functional group (s) (e.g., hydroxyl or vinyl) which may be crosslinked with the resin, such that the coefficient of thermal expansion of the laminate made from the resin composition is reduced.

2. The reactive functional group of the vinyl-containing phosphaphenanthrene-based compound of the present invention is the vinyl group, so that the peroxide may be reacted with other compounds having vinyl functional group (s). In addition, the vinyl ether group has a symmetrical structure and less polarity of functional group compared to the hydroxyl group, thus it may have lower dielectric properties.

3. The present invention vinylates the hydroxyl group to form a vinyl-substituted ether group or a vinyl-substituted ester group, so as to further improve the solubility of the phosphaphenanthrene-based compound in various solvents. Accordingly, the vinyl-containing phosphaphenanthrene-based compound may be soluble in both polar and non-polar solvents better, and the problems such as precipitation of the vinyl-containing phosphaphenanthrene-based compound and low process yield due to poor solubility are avoided.

4. Compared to the oxygen atom with single bond of the vinyl-substituted ether group directly connected to the carbon atom on the aromatic ring, the oxygen atom with single bond of the vinyl-substituted ether group or the vinyl-substituted ester group in the vinyl-containing phosphaphenanthrene-based compound of the present invention is connected to the aromatic ring via the methine group. As such, the laminate made from the cured resin composition having the vinyl-containing phosphaphenanthrene-based compound is more flexible and the problem of brittleness is improved. Furthermore, the vinyl-containing phosphaphenanthrene-based compound of the present invention has the advantage of low water absorption.

These and other objectives of the present invention will no doubt become obvious to those of ordinary skill in the art after reading the following detailed description of the preferred embodiment that is illustrated in the various figures and drawings.

DETAILED DESCRIPTION

In order to verify the characteristics of the phosphaphenanthrene-based compound and related preparation method and applications, embodiments of the present invention are listed below as examples. Those skilled in this art may easily understand the benefits and effects that can be achieved by the present invention via the content of this specification, and may make various modifications without departing from the spirit of the present invention.

The chemicals for use in the embodiments are as follows:

1. Methacrylate-terminated bisphenol A polyphenylene ether resin, available from Sabic under the trade name SA-9000.

2. Vinylbenzyl-terminated biphenyl polyphenylene ether resin, available from Mitsubishi Gas Chemical under the trade name OPE-2st.

3. Bisphenol A cyanate ester resin, available from Lonza under the trade name of BA-230S.

4. Cyanate ester resin, available from Lonza under the trade name of BTP-6020S.

5. Phenylmethane maleimide, available from Japan Daihachi Chemical under the trade name of BMI-2300.

6. Bis (3-ethyl-5-methyl-4-maleimidophenyl) methane), available from KI Chemical under the trade name of BMI-70.

7. 2,5-dimethyl-2,5-di(tert-butylperoxy)-3-hexyne, available from Nippon Oils & Fats under the trade name of 25B.

8. Phosphazene, available from Otsuka Chemical under the trade name of SPB-100.

9. Resorcinol bis [di (2,6-dimethylphenyl) phosphate], available from Japan Daihachi Chemical under the trade name of PX-200.

10. Fused silica, available from Sibelco under the trade name of fused silica.

11. Diethyl aluminum phosphate (organophosphates), available from Clariant under the trade name of OP-935.

12. DOPO bisphenol A novolac hardener, available from Dow Chemical under the trade name of XZ92741.

13. 9,10-dihydro-9-oxa-10-phosphaphenanthrene-10-oxide (DOPO), available from Sanko.

14. 2-(10H-9-oxa-10-phospha-1-phenanthryl) hydroquinone phosphorus oxide, abbreviation as DOPO-HQ, available from Sanko.

15. Zinc octoate, available from Kingyorker.

Embodiment 1: Preparation of Phosphaphenanthrene-Based Compound 500 ml of toluene, 0.4 mol (approximately 78.64 g) of DOPO and 0.2 mol of 1,4-phthalaldehyde (about 26.82 g) are placed in a 1000 ml the three-necked flask equipped with a thermometer and a condenser and are heated and stirred for 5 hours under a reflux environment. The solution is cooled to room temperature, filtered off and dried under vacuum, then a white powder is obtained. The yield is 87.6%.

Figure 1:
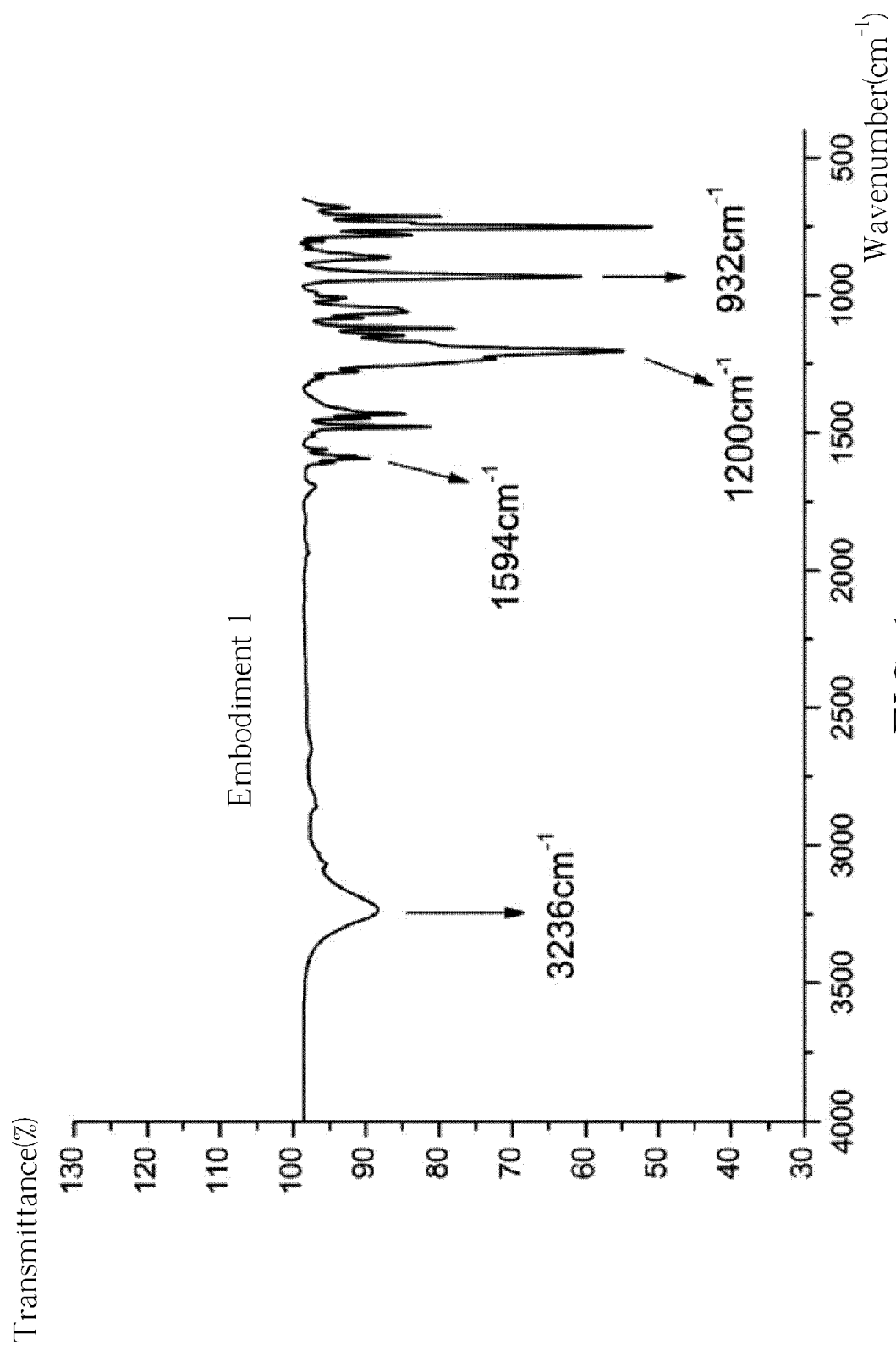
FIG. 1 shows a FTIR spectrum of a phosphaphenanthrene-based compound having a hydroxyl group according to a first embodiment of the present invention.
Figure 2A:
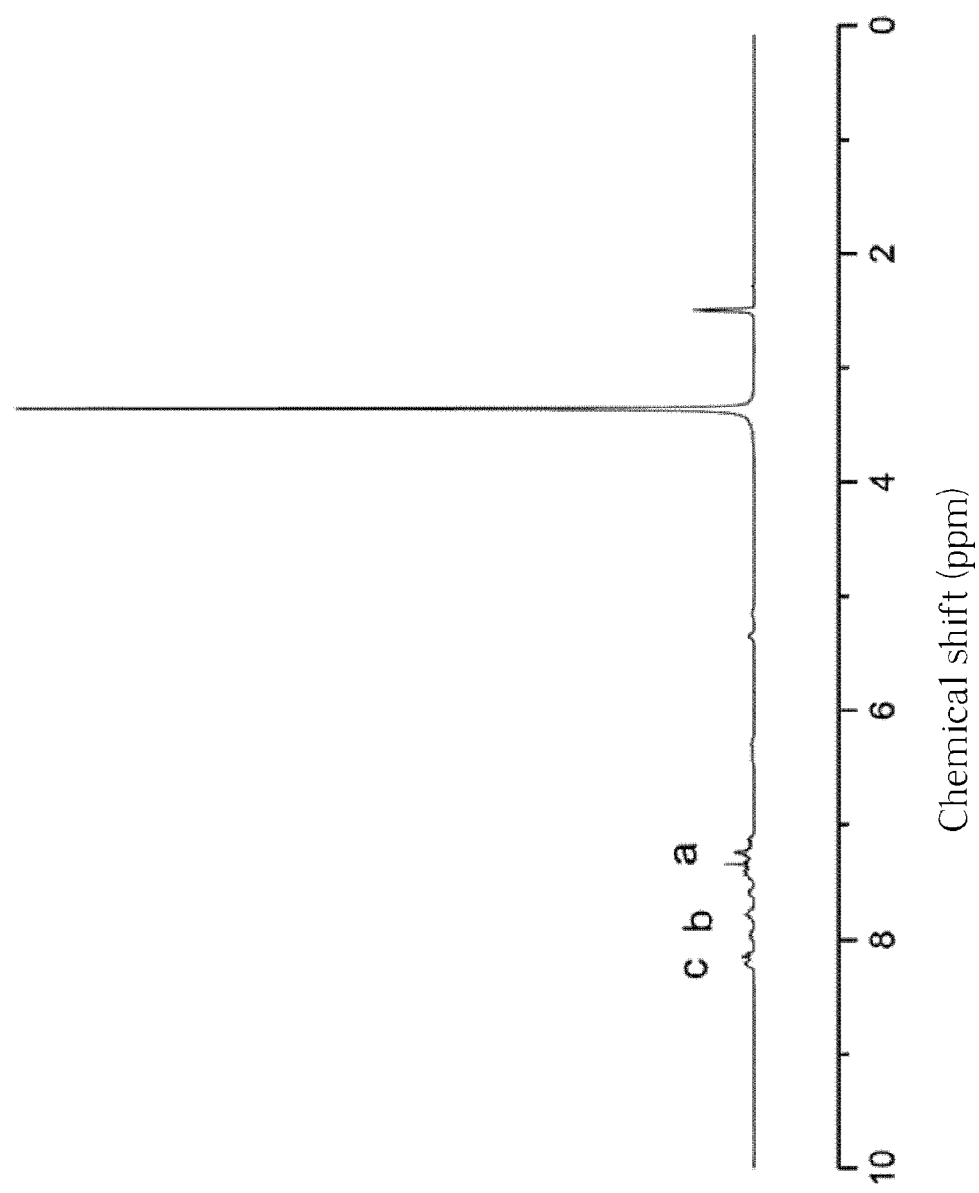
FIG. 2A shows a $^1$H-NMR spectrum of the phosphaphenanthrene-based compound having a hydroxyl group according to the first embodiment of the present invention.
Figure 2B:
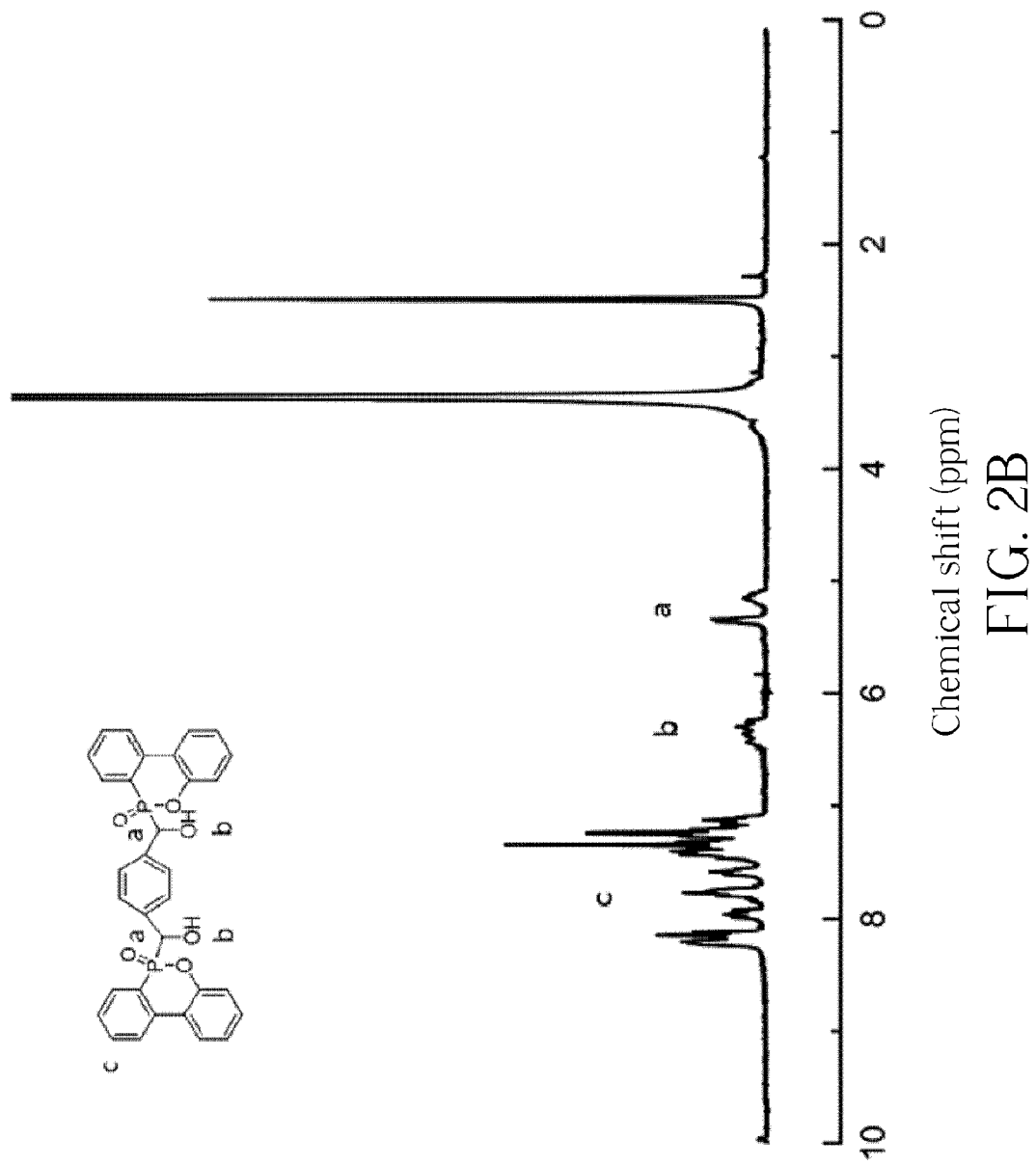
FIG. 2B shows a partially enlarged diagram of the ¹H-NMR spectrum of FIG. 2A.

The obtained white powder is analyzed by the reflection-type Fourier transform infrared spectroscopy (FTIR), and the result is shown in FIG. 1. The FTIR spectrum reveals peaks indicative of a CH—OH at 3236 cm$^{-1}$, a P-Ph at 1594 cm$^{-1}$, a P=O at 1200 cm$^{-1}$ and a PO-Ph at 932 cm$^{-1}$. The obtained white powder is further analyzed by the hydrogen nuclear magnetic resonance spectroscopy (¹H-NMR, 300 MHz, DMSO), and the result is shown in FIG. 2A and FIG. 2B. The ¹H-NMR spectrum reveals peaks indicative of a —CH-Ph at δ=5.1-5.5 ppm (i.e., the position "a" in FIG. 2B), a —OH at δ=6.3-6.5 ppm (i.e., the position "b" in FIG. 2B), and a hydrogen on a benzene ring at δ=7.4-8.4 ppm (i.e., the position "c" in FIG. 2B). In summary, from the analysis results of the FTIR and ¹H-NMR, it is convinced that the white powder has a structure expressed by formula (VIII) below.

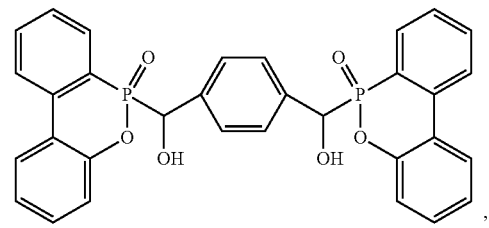

Formula (VIII)

Figure 3:
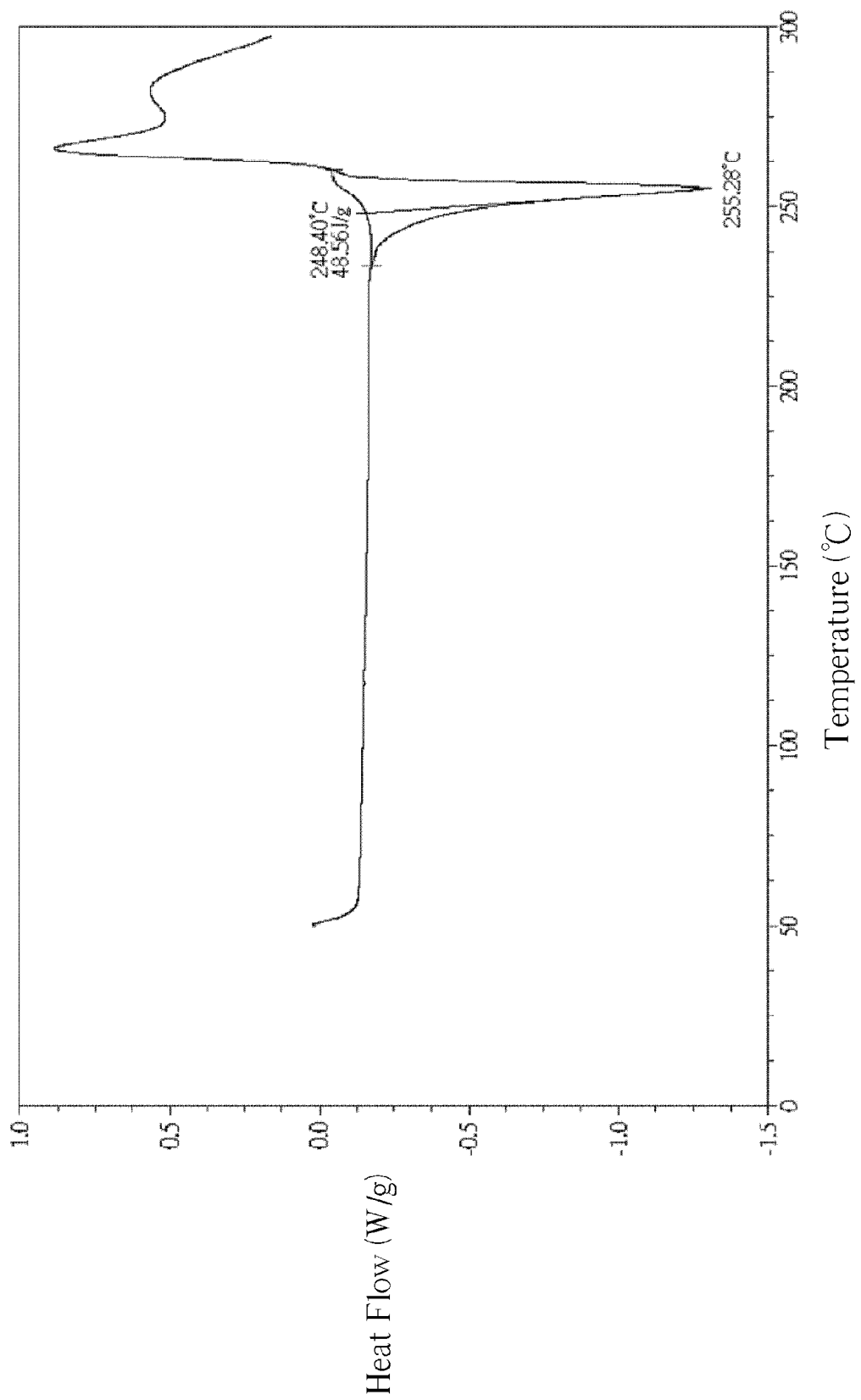
FIG. 3 shows an analysis diagram of the melting point of the phosphaphenanthrene-based compound having a hydroxyl group according to the first embodiment of the present invention.

Further, the white powder is analyzed by a differential scanning calorimeter (DSC) and the observed melting point of the white powder is 248.4 t, wherein the result is shown in FIG. 3. Compared with the conventional commercially available phosphazene compound (SPB-100) with a melting point of 110° C., resorcinol bis [di (2,6-dimethylphenyl) phosphate] (PX-200) with a melting point of 105° C., and phosphorus-containing novolac resin (e.g., DOPO bisphenol A novolac resin) which is a liquid-state resin at room temperature, the phosphaphenanthrene-based compound of the present embodiment (as shown in formula (VIII)) has a higher melting point.

In addition, about 5 grams per serving of the phosphaphenanthrene-based compound are weighed and added to about 30 ml of solvents respectively. Stir with or without heating the solution to dissolve the solute. Observe the dissolution of the phosphaphenanthrene-based compound in different solvents, and the results are shown in Table 1, wherein the numeral "1" represents "easily soluble", which means the solute is dissolved with stirring at room temperature and the solution is clear; the numeral "2" represents "soluble", which means the solute is dissolved with stirring when being heated up to 120° C. and the solution is clear; the numeral "3" represents "insoluble", which means the solute is not dissolve even being heated and stirred.

TABLE 1

The dissolution of the phosphaphenanthrene-based compound (with the structure of formula (VIII)) in different solvents

| Solvent | Dissolution |
| --- | --- |
| Dimethylacetamide (DMAC) | 3 |
| Proprylene glycol monomethyl ether (PM) | 3 |
| Cyclohexanone (CYC) | 3 |
| Methyl ethyl ketone (MEK) | 3 |

TABLE 1-continued

The dissolution of the phosphaphenanthrene-based compound (with the structure of formula (VIII)) in different solvents

| Solvent | Dissolution |
| --- | --- |
| 1-Methoxy-2-propyl acetate (PMA) | 3 |
| Toluene (TL) | 3 |
| N,N-Dimethylformamide (DMF) | 2 |
| Methanol (MT) | 3 |

Embodiment 2: Preparation of Phosphaphenanthrene-Based Compound 500 ml of toluene, 0.4 mol (approximately 78.64 grams) of DOPO and 0.2 mol of 1,4-phthalaldehyde (about 26.82 g) are placed in a 1000 ml three-necked flask equipped with a thermometer and a condenser and are heated and stirred for 5 hours under a reflux environment. The solution is cooled to room temperature, filtered off and dried under vacuum, and then a white powder is obtained. The yield is 91.5%. From the analysis results of the FTIR and $^1$H-NMR, it is convinced that the white powder has a structure expressed by formula (VIII) above.

Then, add 0.5 mol of the white powder and 1.5 mol of sodium hydroxide to a four-necked flask with 1 liter of toluene. Next, heat the solution up to 70° C. and stir it for 30 minutes. Subsequently, add 1.5 mol of 4-chloro-methyl styrene and 0.1 mol of tetrabutylammonium bromide to the solution. Stir for 10 hours. After the reaction is completed and the solution is cooled to room temperature, the solution is filtered off, washed with toluene several times, and dried for 10 hours. A product is obtained with a yield of 80.9%.

Figure 4:
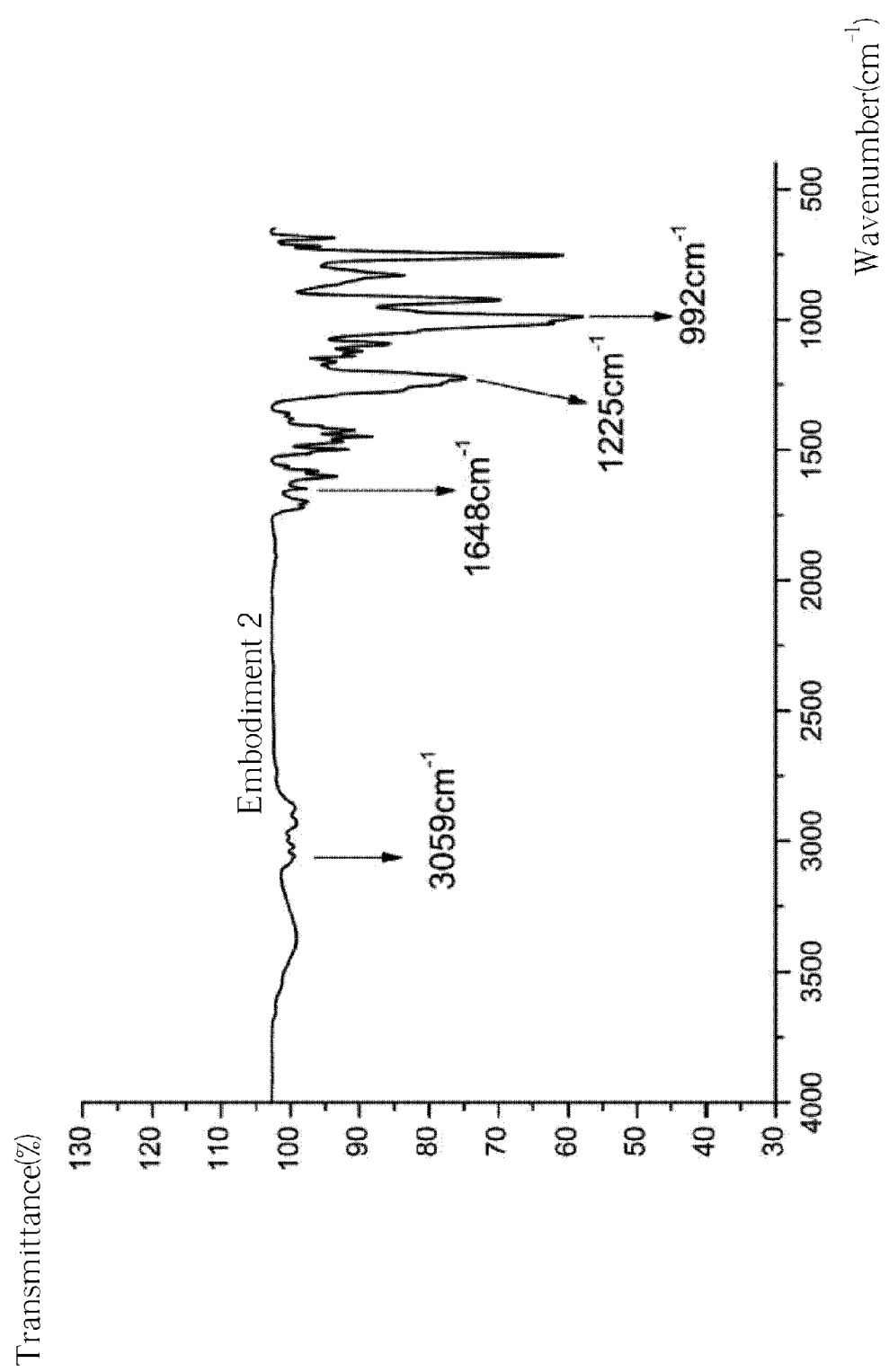
FIG. 4 shows a FTIR spectrum of a vinyl-containing phosphaphenanthrene-based compound according to a second embodiment of the present invention.
Figure 5:
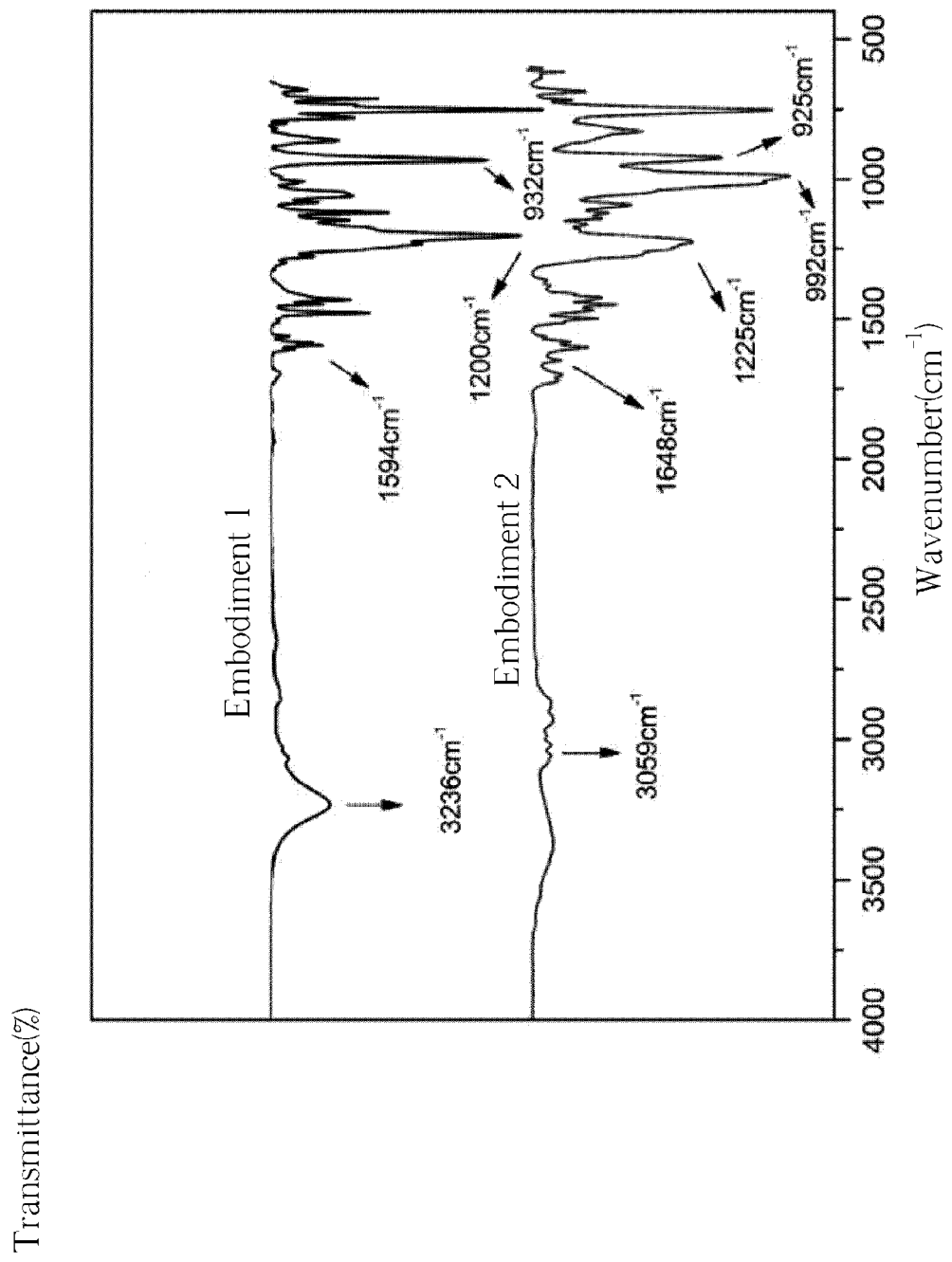
FIG. 5 shows a comparison of the FTIR spectrums of the phosphaphenanthrene-based compound having a hydroxyl group according to the first embodiment and the vinyl-containing phosphaphenanthrene-based compound according to the second embodiment.

The aforementioned product is analyzed by the reflection-type FTIR, and the result is shown in FIG. 4. The FTIR spectrum reveals peaks indicative of a =C—H at 3059 cm$^{-1}$, a —C=C— at 1648 cm$^{-1}$, a C—O—C at 1225 cm$^{-1}$, a —CH=CH$_2$ at 992 cm$^{-1}$ and a P—O-Ph at 925 cm$^{-1}$, wherein the peaks of P=O and C—O—C are overlapped, so the peak shape formed at 1225 cm$^{-1}$ is wider. As shown in FIG. 4 and FIG. 5, the methyl styrene group successfully substitutes the hydrogen atoms of the hydroxyl groups in the aforementioned formula (XVI), so as to form the methyl styrene ether group. As such, it is convinced that the obtained product has a structure expressed by formula (XVI) below.

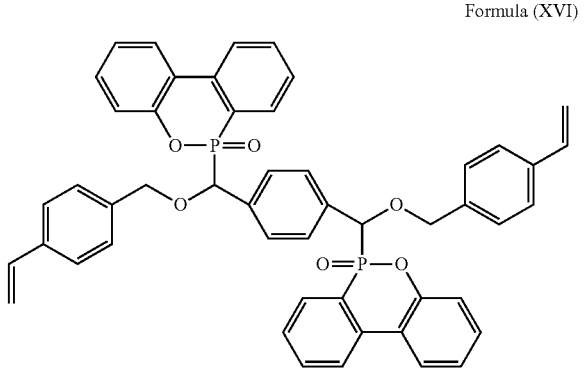 [SMILES: C=Cc1ccc(COC(c2ccc(C(OCc3ccc(C=C)cc3)P3(=O)Oc4ccccc4-c4ccccc43)cc2)P2(=O)Oc3ccccc3-c3ccccc32)cc1]

Formula (XVI)

In addition, about 5 grams per serving of the phosphaphenanthrene-based compound (as shown in formula (XVI)) are weighed and added to about 30 ml of solvents respectively. Stir with or without heating to dissolve the solute. Observe dissolution of the phosphaphenanthrene-based compound in different solvents, and the results are shown in Table 2, wherein the numeral "1" represents "easily soluble", which means the solute is dissolved with stirring at room temperature and the solution is clear; the numeral "2" represents "soluble", which means the solute is dissolved with stirring when being heated up to 120 t and the solution is clear; the numeral "3" represents "insoluble", which means the solute is not dissolve even being heated and stirred.

TABLE 2

The dissolution of the phosphaphenanthrene-based compound (with the structure of formula (XVI)) in different solvents

| Solvent | Dissolution |
| --- | --- |
| Dimethylacetamide | 1 |
| Methyl ethyl ketone | 2 |
| Toluene | 1 |
| Dimethylformamide | 1 |

From the comparison of the result in Table 1 and Table 2, with the introduction of methyl styene group to the phosphaphenanthrene-based compound with the aforementioned formula (VIII), the solubility of the phosphaphenanthrene-based compound can be enhanced, such that the phosphaphenanthrene-based compound with the aforementioned formula (XVI) has good solubility in various solvents.

Comparison 1: The Conventional Phosphaphenanthrene-Based Compound

Add 0.5 mol of the DOPO-HQ (available from Nu tech fine chemical) and 1.5 mol of sodium hydroxide to a four-necked flask with 1 liter of toluene. Next, heat the solution up to 70° C. and stir it for 30 minutes. Subsequently, add 1.5 mol of 4-chloro-methyl styrene and 0.1 mol of tetrabutylammonium bromide to the solution. Stir for 10 hours. After the reaction is completed, cool the system to room temperature, filter the solution and wash with toluene several times, and dry for 10 hours to obtain a compound shown below, a yield of which is 65%.

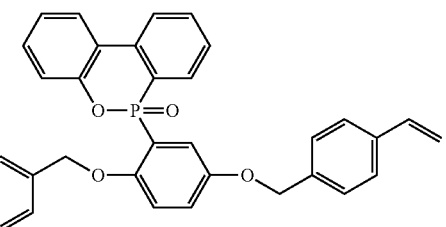

Comparison 2: The Conventional Phosphaphenanthrene-Based Compound

Add 1.5 mol DOPO (available from Nu tech fine chemical) and 1 liter of toluene to a glass reactor equipped with a mechanical stirrer, a condenser, a thermometer and nitrogen protection, stir with heating up to 70° C. Then, add 0.6 mol of 4,4'-diphenoquinone (DQ) (purchased from J & K Technology Co., Ltd.). After stirring for 2 hours at 70° C., cool the solution to room temperature. The solution is filtered off and washes with toluene several times, and dried for 10 hours to obtain a white DOPO biphenol. A yield is 69%. The DOPO biphenol has a structure as shown below.

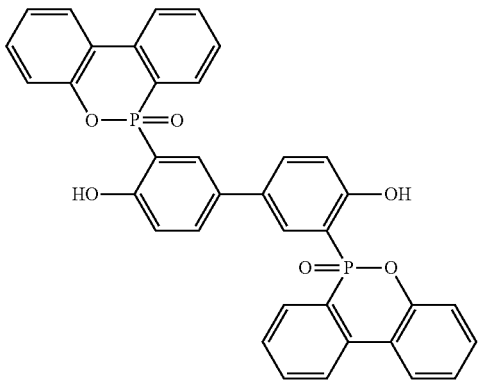 [SMILES: O=P1(c2cc(-c3ccc(O)c(P4(=O)Oc5ccccc5-c5ccccc54)c3)ccc2O)Oc2ccccc2-c2ccccc21]

Then, add 0.5 mol of DOPO biphenol and 1.5 mol of potassium hydroxide to a four-necked flask with 1 liter of toluene. Heat the solution to 70 t and stir it for 30 min. Then, add 1.5 mol of methyl 4-chloromethyl styrene and 0.1 mol of tetrabutylammonium bromide. Stir for 10 hours. After the reaction is completed, cool the solution to room temperature. The solution is filtered off and washed with toluene several times, and dried for 10 hours to obtain a product shown below. A yield is 58%.

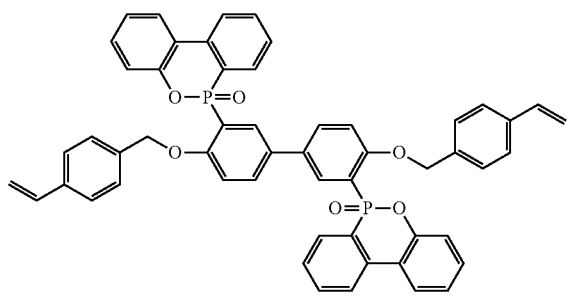 [SMILES: C=Cc1ccc(COc2ccc(-c3ccc(OCc4ccc(C=C)cc4)c(P4(=O)Oc5ccccc5-c5ccccc54)c3)cc2P2(=O)Oc3ccccc3-c3ccccc32)cc1]

From the results of the embodiments 1 to 2 and comparisons 1 to 2 above, it infers that under the same synthesis conditions, the phosphaphenanthrene-based compound of the embodiments 1 to 2, by the way of changing the chemical structure, have higher yield than the conventional phosphaphenanthrene-based compounds.

Test Example 1: Solvent Compatibility

The phosphaphenanthrene-based compound of the embodiment 2, the conventional phosphaphenanthrene-based compound of the comparison 1 and the conventional phosphaphenanthrene-based compound of the comparison 2 are used as test samples of the test example 1. The test samples are respectively dissolved in toluene, methyl ethyl ketone, and acetone, so as to give a test to the compatibilities of the test samples in these solvents. The results observed by naked eyes are shown in Table 3.

TABLE 3

The test results of compatibilities of the phosphaphenanthrene-based compound of the embodiment 2 and the conventional phosphaphenanthrene-based compounds of the comparison 2 in different solvents

| Solvent | Observation time | Embodiment 2 | Comparison 1 | Comparison 2 |
|---|---|---|---|---|
| Toluene | The initial state | Soluble, clear light yellow solution | Soluble, clear light yellow solution | Soluble, clear light yellow solution |
| | Stand for 12 hours | No precipitation, clear light yellow solution | No precipitation, clear light yellow solution | No precipitation, clear light yellow solution |
| Methyl ethyl ketone | The initial state | Soluble, clear light yellow solution | Soluble, clear light yellow solution | Soluble, clear light yellow solution |
| | Stand for 12 hours | No precipitation, clear light yellow solution | Precipitated with white educt, cloudy solution with white precipitate at the vessel bottom | Precipitated with white educt, cloudy solution with white precipitate at the vessel bottom |
| Acetone | The initial state | Soluble, clear light yellow solution | Soluble, clear light yellow solution | Soluble, clear light yellow solution |
| | Stand for 12 hours | No precipitation, as a clear light yellow solution | Precipitated with white educt, cloudy solution with white precipitate at the vessel bottom | Precipitated with white educt, cloudy solution with white precipitate at the vessel bottom |

As shown in Table 3, the phosphaphenanthrene-based compound of the embodiment 2 is soluble in toluene, methyl ethyl ketone and acetone, and no white educt would appear after being placed for 12 hours, which shows that the phosphaphenanthrene-based compound of the embodiment 2 has good compatibility with toluene, methyl ethyl ketone and acetone. Conversely, though the conventional phosphaphenanthrene-based compounds of the comparison 1 to 2 are soluble in methyl ethyl ketone and acetone, apparent white educts can be observed by naked eyes and are appeared at the bottom of the vessels after standing for 12 hours.

Toluene, methyl ethyl ketone and acetone or a combination thereof are commonly used in the production process of prepregs. To dissolve the phosphaphenanthrene-based compound of the embodiment 2 in ketone solvents does not cause precipitation problems. On the contrary, when the conventional phosphaphenanthrene-based compounds of the comparisons 1 to 2 are selected to be dissolved in ketone solvents, educts will appear and thus the conventional phosphaphenanthrene-based compounds have disadvantages of bring unstable quality and lower flame retardancy.

From the above comparison results, the phosphaphenanthrene-based compound of the present invention has better compatibility with ketone solvents than the conventional phosphaphenanthrene-based compounds. In addition, no educt would appear after the solution is placed for a period of time, such that the quality and flame retardancy of the phosphaphenanthrene-based compound of the present invention are assured.

Embodiment 3: Preparation of Resin Composition Containing Phosphaphenanthrene-Based Compound According to the ratio listed in Table 4, the phosphaphenanthrene-based compound prepared in the embodiment 1 (as shown in formula (VIII)) and the phosphaphenanthrene-based compound prepared in the embodiment 2 (as shown in formula (XVI)) are respectively adequately mixed with polyphenylene ether resin, cyanate ester resin, maleimide, flame retardants, inorganic fillers, curing accelerator and solvent to form resin compositions having the phosphaphenanthrene-based compound, i.e., example 1 to example 12 (hereinafter denoted as E1 to E12).

Comparison 3: Preparation of Resin Composition

According to the ratio listed in Table 5, the phosphaphenanthrene-based compound prepared in the embodiment 1 (as shown in formula (VIII)) and the phosphaphenanthrene-based compound prepared in the embodiment 2 (as shown in formula (XVI)) are selectively mixed with polyphenylene ether resin, cyanate ester resin, maleimide, flame retardants, inorganic fillers, curing accelerator and solvent adequately to form resin compositions of comparative example 1 to comparative example 13 (hereinafter denoted as C1 to C13) by fully mixing each component in Table 5. Wherein, none of the phosphaphenanthrene-based compounds formed according to the embodiment 1 to 2 are mixed in the resin compositions of C1 to C3, C6 to C8 and C11 to C13 do not mix with.

Test Example 2: Analysis of the Properties of Resin Composition

The resin compositions having the phosphaphenanthrene-based compounds in E1 to E12 and the resin compositions in C1 to C13 are selected in this test example. Each selected resin composition is evenly mixed in a blender by batch before being put into an impregnation tank respectively. Then, a glass fiber fabric (the specification of E-glass fiber fabric is 2116, available from Nan Ya Plastics Industry) is immersed into the impregnation tank to allow the resin composition to adhere to the glass fiber fabric before undergoing a heat baking process under 120° C.-160° C. to become semi-cured, thereby forming a prepreg.

Preparation of the Test Samples for Property Analysis:

1. Copper-Clad Laminate:

The copper-clad laminate of each of the aforementioned test sample is prepared in the following. Two pieces of copper foils with a thickness of 18 μm, and four pieces of the prepregs manufactured according to the selected test sample are supplied, wherein each prepreg has a thickness of 0.127 mm. The content of the resin of each prepreg is about 55%. The copper foil, four pieces of the prepregs and copper foil are stacked in sequence before being laminated against each other under vacuum at 210° C. for two hours to form a copper-clad laminate, wherein, the stacked four pieces of prepregs are cured to form an insulating layer between the two copper foils, and the content of the resin of the insulating layer is about 55%.

2. Copper-Free Laminate (Four Plies):

The aforementioned copper-clad laminate is etched to remove the two copper foils to obtain the copper-free laminate (four plies). Wherein the copper-free laminate (four plies) are formed with four laminated prepregs, and the content of the resin of the copper-free laminate (four plies) is about 55%.

3. Copper-Free Laminate (Double Plies):

Two pieces of copper foils with a thickness of 18 μm and two pieces of the prepregs manufactured according to the selected test samples mentioned above are supplied, wherein each of the prepregs has a thickness of 0.127 mm. The content of the resin of each prepreg is about 55%. The copper foil, two pieces of the prepreg and copper foil are stacked in sequence before being laminated against each other under vacuum at 210° C. for two hours to form a double plies copper-clad laminate.

Next, the double plies copper-clad laminate undergoes etching to remove the two copper foils so as to obtain the copper-free laminate (double plies). Wherein the insulating laminate is formed with two laminated prepregs, and the content of the resin of the copper-free laminate (double plies) is about 55%.

The property analysis of this test example includes the following items.

1. Glass transition temperature (Tg):

To measure the glass transition temperature, the copper-free laminate (four plies) is selected as the test sample. The glass transition temperature of each test sample is measured by a dynamic mechanical analysis (DMA) according to IPC-TM-650 2.4.24.4 test method.

2. Coefficient of thermal expansion (CTE z-axis):

To measure the coefficient of thermal expansion, the copper-free laminate (four plies) is selected as the test sample. The coefficient of thermal expansion of each test samples is measured by a thermal mechanical analyzer (TMA) according to IPC-TM-650 2.4.24.5 test method, wherein the unit is ppm/° C. A lower coefficient of thermal expansion indicates that the expansion proportion of the test sample under heating is smaller, which means the resin composition has better properties when it is applied to the printed circuit board.

3. Solder dipping (S/D):

To measure the solder dipping, the copper-clad laminate (four plies) is selected as the test sample. Each test sample is immersed in the solder pot with a constant temperature of 288° C. for 10 seconds each time. Repeat the step above to test the total cycle of heat resistance without delamination of each test sample. the more total cycle of the test sample indicates that the heat resistance of the copper-clad laminate formed with the resin composition is better.

4. Pressure cooking test (PCT):

In PCT, the copper-free laminate (four plies) is selected as the test sample. Each test sample is placed in an environment with a temperature of 121° C. and a 100% relative humidity to absorb moisture for 3 hours. Then, each test sample is immersed in a solder pot with a constant temperature of 288° C. for 20 seconds to see if any of the test samples delaminates. Pass of test result means no delamination. If the test sample does not rupture after the PCT, the resin composition applied to a printed circuit board has good heat resistance after moisture absorption.

5. Dielectric constant (Dk) and dissipation factor (Df):

To measure the dielectric constant and dissipation factor, the copper-free laminate (double plies) is selected as the test sample, measured at 10 GHz by a microwave dielectrometer (purchased from AET) according to JIS C2565 test method. The lower dielectric constant and lower dissipation factor indicates that the dielectric properties of the test sample are better.

6. Flame retardancy:

In the flame retardancy test, the copper-free laminate (four plies) is selected as the test sample. The flame resistance test is performed according to UL94 test method, and the analysis results are illustrated in the rankings V-0, V-1, and V-2, wherein the ranking V-0 is superior to V-1 and V-1 is superior to V-2.

The results of measurement of the test samples prepared by the resin compositions having the phosphaphenanthrene-based compounds in embodiments E1 to E12 are enumerated in Table 6. The results of measurement of the test samples prepared by the resin compositions in comparisons C1 to C13 are enumerated in Table 7.

TABLE 4

The ratio of the resin composition having the phosphaphenanthrene-based compound in E1 to E12 (unit: parts by weight)

| Component | | E1 | E2 | E3 | E4 | E5 | E6 |
|---|---|---|---|---|---|---|---|
| Polyphenylene ether resin | OPE-2st | 50 | 50 | 50 | 50 | 50 | 50 |
| | SA-9000 | 50 | 50 | 50 | 50 | 50 | 50 |
| Cyanate resin | BA-230S | 10 | 10 | 10 | 0 | 0 | 0 |
| | BTP-6020S | 10 | 10 | 10 | 20 | 20 | 0 |
| Maleimide | BMI-2300 | 10 | 10 | 10 | 20 | 20 | 10 |
| | BMI-70 | 10 | 10 | 10 | 0 | 0 | 10 |
| Phosphaphenanthrene-based compound | Embodiment 1 | 55 | 0 | 0 | 45 | 0 | 40 |
| | Embodiment 2 | 0 | 55 | 70 | 0 | 45 | 0 |
| Flame retardant | OP-935 | 0 | 0 | 0 | 0 | 0 | 0 |
| Inorganic filler | Fused silica | 40 | 40 | 40 | 40 | 40 | 40 |
| Solvent | MEK | 30 | 30 | 30 | 30 | 30 | 30 |
| | Toluene | 30 | 30 | 30 | 30 | 30 | 30 |
| Curing accelerator | Zinc octoate | 0.03 | 0.03 | 0.03 | 0.03 | 0.03 | 0.03 |
| | 25B | 1 | 1 | 1 | 1 | 1 | 1 |

| Component | | E7 | E8 | E9 | E10 | E11 | E12 |
|---|---|---|---|---|---|---|---|
| Polyphenylene ether resin | OPE-2st | 50 | 50 | 50 | 80 | 70 | 50 |
| | SA-9000 | 50 | 50 | 50 | 70 | 30 | 50 |
| Cyanate resin | BA-230S | 0 | 10 | 10 | 5 | 5 | 10 |
| | BTP-6020S | 0 | 10 | 10 | 5 | 5 | 10 |
| Maleimide | BMI-2300 | 10 | 10 | 10 | 20 | 10 | 10 |
| | BMI-70 | 10 | 10 | 10 | 20 | 20 | 10 |
| Phosphaphenanthrene-based compound | Embodiment 1 | 0 | 20 | 0 | 0 | 0 | 0 |
| | Embodiment 2 | 40 | 0 | 10 | 100 | 55 | 112 |
| Flame retardant | OP-935 | 0 | 7 | 10 | 0 | 0 | 0 |
| Inorganic filler | Fused silica | 40 | 40 | 40 | 60 | 40 | 40 |
| Solvent | MEK | 30 | 30 | 30 | 30 | 30 | 30 |
| | Toluene | 30 | 30 | 30 | 70 | 30 | 30 |
| Curing accelerator | Zinc octoate | 0.03 | 0.03 | 0.03 | 0.03 | 0.03 | 0.03 |
| | 25B | 1 | 1 | 1 | 1 | 1 | 1 |

TABLE 5

The ratio of the resin composition in C1 to C13 (unit: parts by weight)

| Component | | C1 | C2 | C3 | C4 | C5 | C6 | C7 |
|---|---|---|---|---|---|---|---|---|
| Polyphenylene ether resin | OPE-2st | 50 | 50 | 50 | 50 | 50 | 50 | 50 |
| | SA-9000 | 50 | 50 | 50 | 50 | 50 | 50 | 50 |
| Cyanate resin | BA-230S | 10 | 10 | 10 | 10 | 10 | 10 | 10 |
| | BTP-6020S | 10 | 10 | 10 | 10 | 10 | 10 | 10 |
| Maleimide | BMI-2300 | 10 | 10 | 10 | 10 | 10 | 10 | 10 |
| | BMI-70 | 10 | 10 | 10 | 10 | 10 | 10 | 10 |
| Phosphaphenanthrene-based compound | Embodiment 1 | 0 | 0 | 0 | 5 | 0 | 0 | 0 |
| | Embodiment 2 | 0 | 0 | 0 | 0 | 5 | 0 | 0 |
| Flame retardant | OP-935 | 0 | 0 | 0 | 0 | 0 | 27 | 20 |
| | SPB-100 | 55 | 0 | 0 | 0 | 0 | 0 | 7 |
| | PX-200 | 0 | 55 | 0 | 0 | 0 | 0 | 0 |
| | XZ92741 | 0 | 0 | 55 | 0 | 0 | 0 | 0 |
| | DOPO | 0 | 0 | 0 | 0 | 0 | 0 | 0 |
| | DOPO-HQ | 0 | 0 | 0 | 0 | 0 | 0 | 0 |
| Inorganic filler | Fused silica | 40 | 40 | 40 | 40 | 40 | 40 | 40 |
| Solvent | MEK | 30 | 30 | 30 | 30 | 30 | 30 | 30 |
| | Toluene | 30 | 30 | 30 | 30 | 30 | 30 | 30 |
| Curing accelerator | Zinc octoate | 0.03 | 0.03 | 0.03 | 0.03 | 0.03 | 0.03 | 0.03 |
| | 25B | 1 | 1 | 1 | 1 | 1 | 1 | 1 |

| Component | | C8 | C9 | C10 | C11 | C12 | C13 |
|---|---|---|---|---|---|---|---|
| Polyphenylene ether resin | OPE-2st | 50 | 50 | 50 | 50 | 50 | 70 |
| | SA-9000 | 50 | 50 | 50 | 50 | 50 | 30 |
| Cyanate resin | BA-230S | 0 | 10 | 10 | 10 | 10 | 5 |
| | BTP-6020S | 0 | 10 | 10 | 10 | 10 | 5 |

TABLE 5-continued

The ratio of the resin composition in C1 to C13 (unit: parts by weight)

| | | | | | | | |
|---|---|---|---|---|---|---|---|
| Maleimide | BMI-2300 | 10 | 10 | 10 | 10 | 10 | 10 |
| | BMI-70 | 10 | 10 | 10 | 10 | 10 | 20 |
| Phosphaphenanthrene- | Embodiment 1 | 0 | 150 | 0 | 0 | 0 | 0 |
| based compound | Embodiment 2 | 0 | 0 | 150 | 0 | 0 | 0 |
| Flame retardant | OP-935 | 0 | 0 | 0 | 0 | 0 | 5 |
| | SPB-100 | 0 | 0 | 0 | 0 | 0 | 30 |
| | PX-200 | 0 | 0 | 0 | 0 | 0 | 10 |
| | XZ92741 | 40 | 0 | 0 | 0 | 0 | 5 |
| | DOPO | 0 | 0 | 0 | 55 | 0 | 0 |
| | DOPO-HQ | 0 | 0 | 0 | 0 | 55 | 0 |
| Inorganic filler | Fused silica | 40 | 40 | 40 | 40 | 40 | 40 |
| Solvent | MEK | 30 | 30 | 30 | 30 | 30 | 30 |
| | Toluene | 30 | 30 | 30 | 30 | 30 | 30 |
| Curing accelerator | Zinc octoate | 0.03 | 0.03 | 0.03 | 0.03 | 0.03 | 0.03 |
| | 25B | 1 | 1 | 1 | 1 | 1 | 1 |

TABLE 6

The results of property analysis of the test samples made from the resin composition of E1 to E12

| Property item | E1 | E2 | E3 | E4 | E5 | E6 |
|---|---|---|---|---|---|---|
| Glass transition temperature (° C.) | 205 | 203 | 198 | 207 | 205 | 198 |
| Coefficient of thermal expansion (ppm/° C.) | 49 | 49 | 47 | 51 | 51 | 53 |
| Solder dipping | >20 | >20 | >20 | >20 | >20 | >20 |
| PCT | pass | pass | pass | pass | pass | pass |
| Dielectric constant | 3.75 | 3.65 | 3.71 | 3.74 | 3.64 | 3.71 |
| Dissipation factor | 0.0095 | 0.0068 | 0.0067 | 0.0093 | 0.0065 | 0.0085 |
| Flame retardancy | V-0 | V-0 | V-0 | V-0 | V-0 | V-0 |

| Property item | E7 | E8 | E9 | E10 | E11 | E12 |
|---|---|---|---|---|---|---|
| Glass transition temperature (° C.) | 195 | 208 | 210 | 211 | 206 | 201 |
| Coefficient of thermal expansion (ppm/° C.) | 53 | 55 | 58 | 53 | 49 | 50 |
| Solder dipping | >20 | >20 | >20 | >20 | >20 | >20 |
| PCT | pass | pass | pass | pass | pass | pass |
| Dielectric constant | 3.62 | 3.75 | 3.72 | 3.73 | 3.62 | 3.71 |
| Dissipation factor | 0.0058 | 0.0082 | 0.0070 | 0.0064 | 0.0057 | 0.0066 |
| Flame retardancy | V-0 | V-0 | V-0 | V-0 | V-0 | V-0 |

TABLE 7

The results of property analysis of the test samples made from the resin composition of C1 to C13

| Property item | C1 | C2 | C3 | C4 | C5 | C6 | C7 |
|---|---|---|---|---|---|---|---|
| Glass transition temperature (° C.) | 165 | 145 | 148 | 212 | 212 | 208 | 195 |
| Coefficient of thermal expansion (ppm/° C.) | 66 | 74 | 60 | 49 | 49 | 63 | 63 |
| Solder dipping | 20 | 15 | 4 | >20 | >20 | 15 | 15 |
| PCT | pass | delaminated | delaminated | pass | pass | delaminated | delaminated |
| Dielectric constant | 3.98 | 3.98 | 4.05 | 3.71 | 3.65 | 3.94 | 3.92 |

TABLE 7-continued

The results of property analysis of the test samples made from the resin composition of C1 to C13

| Dissipation factor | 0.0097 | 0.0089 | 0.0115 | 0.0073 | 0.0065 | 0.0108 | 0.0105 |
|---|---|---|---|---|---|---|---|
| Flame retardancy | V-0 | V-1 | V-0 | V-2 | V-2 | V-0 | V-1 |

| Property item | C8 | C9 | C10 | C11 | C12 | C13 |
|---|---|---|---|---|---|---|
| Glass transition temperature (° C.) | 170 | 191 | 201 | 172 | 185 | 188 |
| Coefficient of thermal expansion (ppm/° C.) | 61 | 60 | 58 | 70 | 71 | 60 |
| Solder dipping | 8 | 10 | 15 | 5 | 3 | 18 |
| PCT | delaminated | delaminated | pass | delaminated | delaminated | delaminated |
| Dielectric constant | 4.05 | 4.05 | 3.83 | 4.12 | 4.18 | 3.89 |
| Dissipation factor | 0.0121 | 0.0121 | 0.0068 | 0.0121 | 0.0135 | 0.0085 |
| Flame resistance | V-0 | V-0 | V-0 | V-0 | V-0 | V-0 |

From the results of E1 or E2 in Table 6 compared to any one of the results of C1 to C3 in Table 7, it is convinced that the laminate made from the phosphaphenanthrene-based compound of the present invention has lower coefficient of thermal expansion, higher glass transition temperature, better heat resistance and better heat resistance after moisture absorption.

In particular, when the phosphaphenanthrene-based compound has a vinyl group (E2), the laminate prepared thereof have low dielectric constant and low dissipation factor. As such, the further introduction of the vinyl group effectively improves the dielectric constant and dissipation factor of the laminate. The effects mentioned above may also be seen from comparing E2, E3, E5 and E7 with E1, E4, E6 and E8.

In addition, from the results of E1 or E2 in Table 6 compared to the results of C11 or C12 in Table 7, though the laminate made from the resin composition containing the commercially available flame retardants such as DOPO or DOPO-HQ may have expected flame retardancy, its overall performance (such as heat resistance, heat resistance after moisture absorption and dielectric properties) is poor. On the other hand, the laminate made from the resin composition having the phosphaphenanthrene-based compound of the present invention have advantages such as lower coefficient of thermal expansion, higher heat resistance, higher glass transition temperature and lower dielectric constant and dissipation factor at the same time.

From the results of E6 or E7 in Table 6 compared to the results of C8 in Table 7, it is convinced that the laminate made from the resin composition having the phosphaphenanthrene-based compound of the present invention has lower coefficient of thermal expansion, higher glass transition temperature, better heat resistance and better heat resistance after moisture absorption at the same time.

From the results of E1 in Table 6 compared to the results of C4 in Table 7 and the results of E2 in Table 6 compared to the results of C5 in Table 7, it is convinced that if the content of the phosphaphenanthrene-based compound is too low, the laminate made from the resin composition is hard to have a suitable flame retardancy. In addition, from the results of C9, it is convinced that if the content of the phosphaphenanthrene-based compound in the resin composition is too high, the laminate made from the resin composition is hard to pass the PCT (i.e., delamination), and has disadvantages such as lower glass transition temperature, higher coefficient of thermal expansion, reduced heat resistance and higher dielectric properties. Furthermore, from the results of E12 in Table 6 compared to the results of C10 in Table 7, it is convinced that if the content of the phosphaphenanthrene-based compound of embodiment 2 in the resin composition is too high, the laminate prepared therefrom might pass the PCT (i.e., no delamination), but the laminate may still have problems such as lower glass transition temperature, higher coefficient of thermal expansion, reduced heat resistance and higher dielectric properties.

Further, from the results of E8 compared to the results of E1 and the results of E9 compared to the results of E2, it is convinced that when the phosphaphenanthrene-based compound of the present invention is used with other flame retardants, the laminate made from the resin composition may have similar flame retardancy, dielectric properties, and heat resistance and heat resistance after moisture absorption with a reduced amount of the phosphaphenanthrene-based compound added in the resin composition. However, from the results of E11 in Table 6 compared to the results of C13 in Table 7, it is convinced that though the resin composition doped with a combination of a variety of conventional phosphorus-containing flame retardants, the overall performance of the laminate prepared therefrom is still worse than that of the laminate made from the resin composition having the phosphaphenanthrene-based compound of the present invention. In addition, from the results of E8 compared to the results of C6 or C7, it is convinced that the laminate made from the resin composition containing conventional phosphorus-based flame retardant has higher coefficient of thermal expansion, higher dielectric properties, reduced heat resistance, and unsatisfactory heat resistance after moisture absorption, and the flame retardancy of the laminate is unexpectedly worse than the flame resistance of the laminate made from the resin composition containing the phosphaphenanthrene-based compound of the present invention.

The present invention is disclosed above by preferred embodiments. However, those skilled in the art should understand that the preferred embodiments are illustrative of the present invention only, but should not be interpreted as restrictive of the scope of the present invention. Accordingly, the legal protection for the present invention should be defined by the appended claims, and should not be limited to the aforementioned embodiments.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A phosphaphenanthrene-based compound having a structure expressed by formula (I) below:

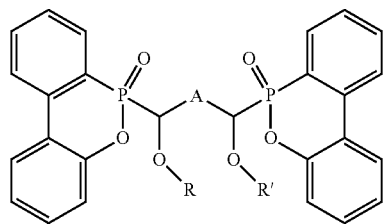

Formula (I)

wherein R and R' are each independently a hydrogen atom, a vinyl-substituted alkyl group with 3 to 20 carbon atoms, a vinyl-substituted cycloalkyl group with 8 to 20 carbon atoms, a vinyl-substituted benzyl group with 9 to 20 carbon atoms, or a vinyl-substituted aromatic functional group with 8 to 20 carbon atoms, a vinyl- and carbonyl-substituted alkyl group with 4 to 20 carbon atoms, a vinyl- and carbonyl-substituted cycloalkyl group with 8 to 20 carbon atoms, a vinyl- and carbonyl-substituted aromatic group with 9 to 20 carbon atoms, a vinyl- and carbonyl-substituted benzyl group with 10 to 20 carbon atoms, or

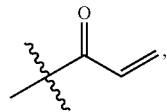 [SMILES: *C(=O)C=C]

wherein at least one of R or R' is not hydrogen; and
A is a covalent bond, a methylene, a cycloalkane-diyl group with 3 to 12 carbon atoms, a cycloalkene-diyl group with 6 to 12 carbon atoms, an alkane-diyl group with 2 to 12 carbon atoms,

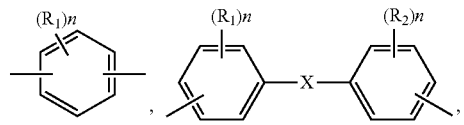

-continued

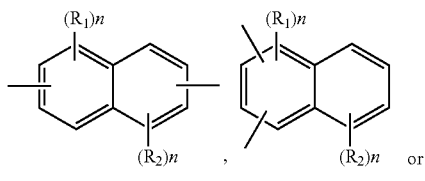

wherein $R_1$ and $R_2$ are each independently an alkyl group with 1 to 3 carbon atoms, X is —$CH_2$—,

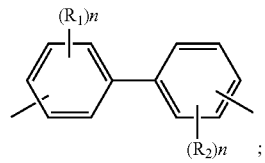

and n is an integer ranging from 0 to 4.

2. The phosphaphenanthrene-based compound according to claim 1, wherein R and R' are each independently a vinyl-substituted alkyl group with 3 to 20 carbon atoms, or a vinyl-substituted benzyl group with 9 to 20 carbon atoms.

3. The phosphaphenanthrene-based compound according to claim 1, wherein R and R' are each independently

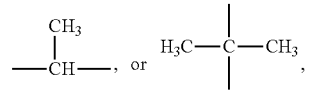

4. The phosphaphenanthrene-based compound according to claim 1, wherein the phosphaphenanthrene-based compound has a structure expressed below:

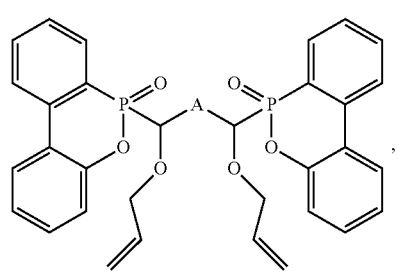

Formula (III)

Formula (IV)
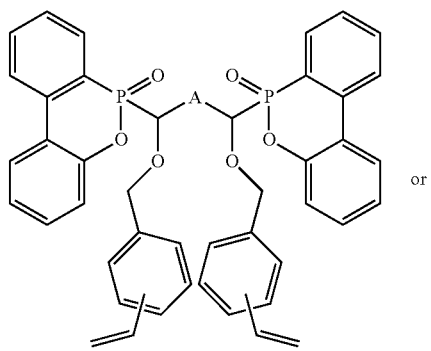
or
Formula (V)
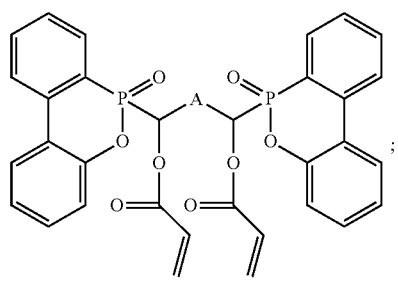
wherein A is
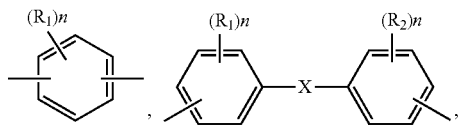
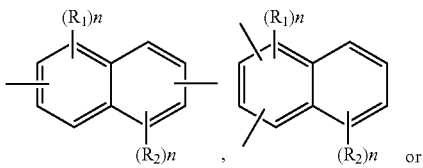
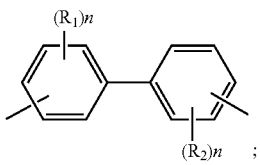
wherein $R_1$ and $R_2$ are each independently an alkyl group with 1 to 3 carbon atoms, X is —$CH_2$—,
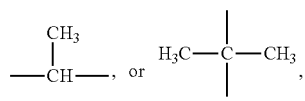
and n is an integer ranging from 0 to 4.
5. The phosphaphenanthrene-based compound according to claim 1, wherein the phosphaphenanthrene-based compound has a structure expressed below:
Formula (XVI)
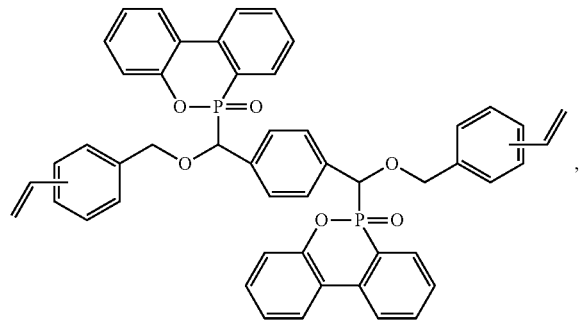
Formula (XVII)
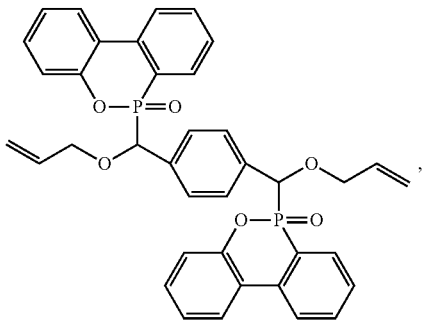
Formula (XVIII)
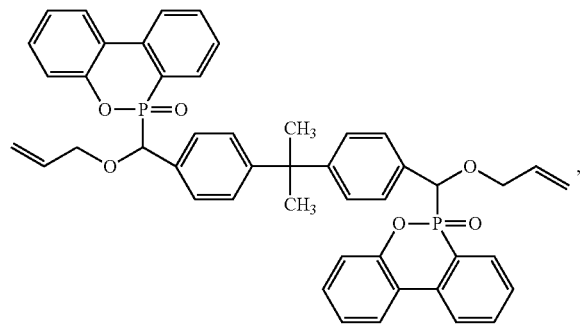
Formula (XIX)
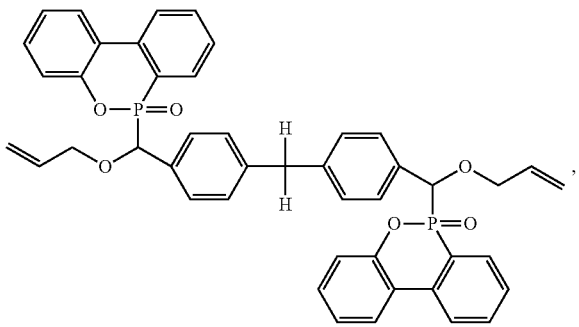

-continued
Formula (XX)
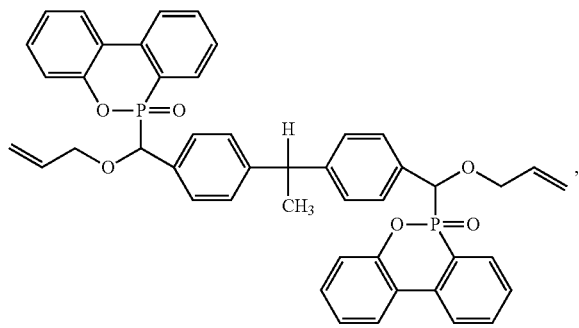
Formula (XXI)
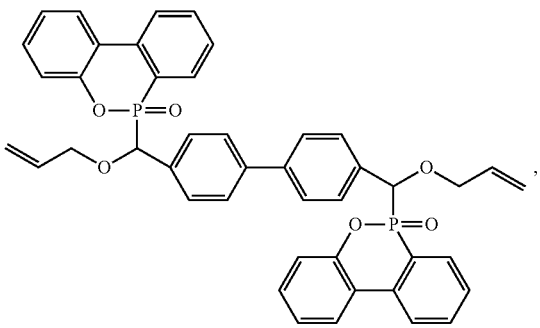
Formula (XXII)
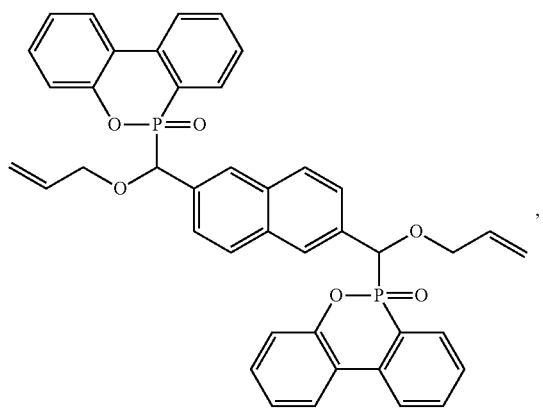
Formula (XXIII)
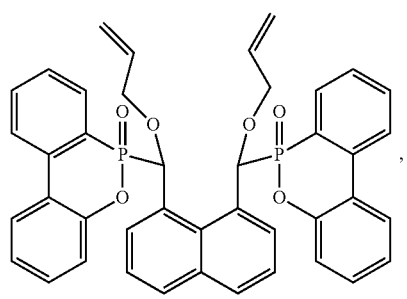
Formula (XXIV)
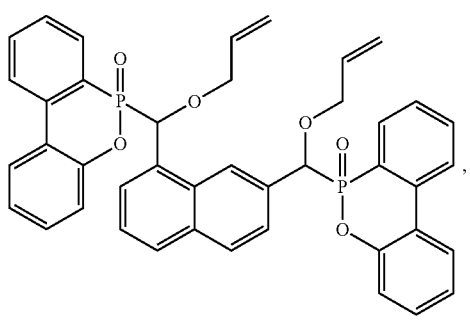
Formula (XXV)
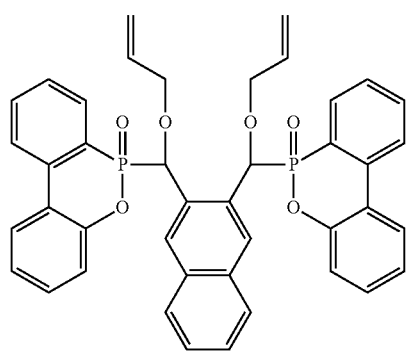
Formula (XXVI)
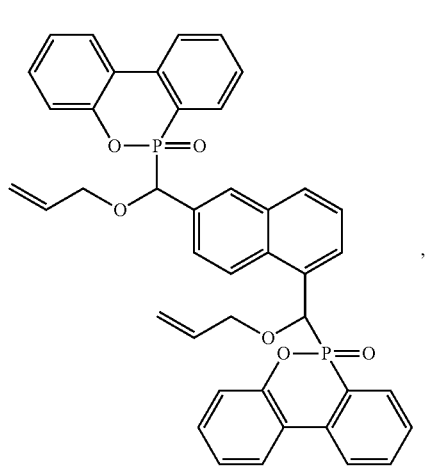

-continued
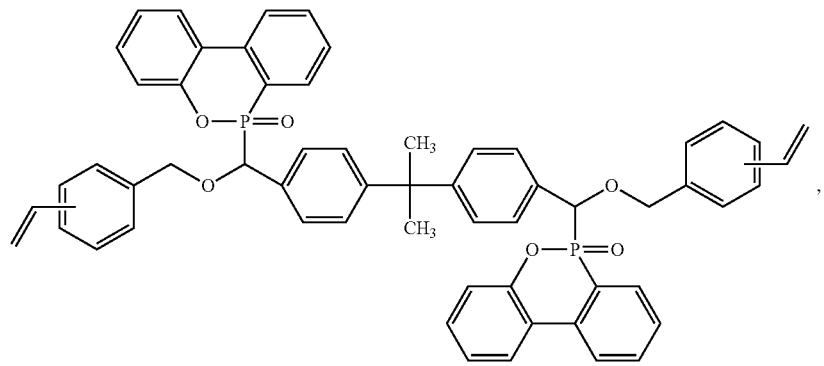
Formula (XXVII)
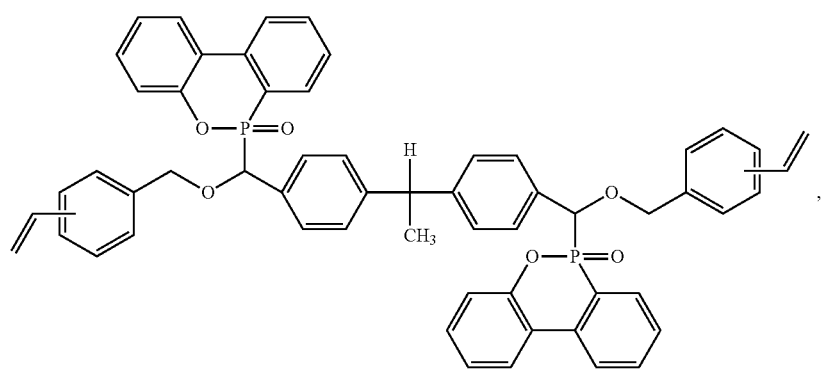
Formula (XXVIII)
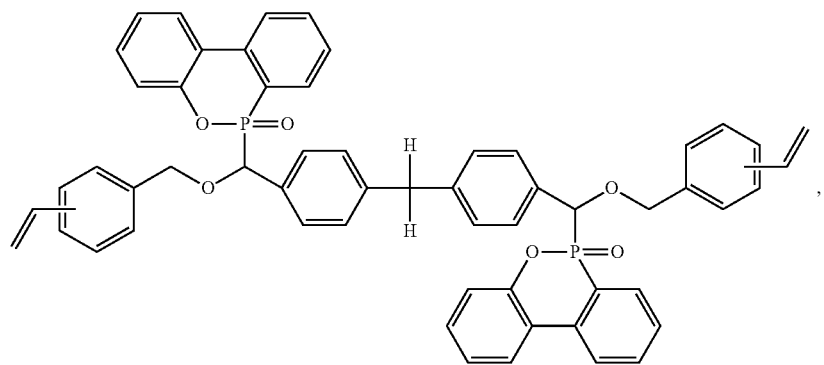
Formula (XXIX)
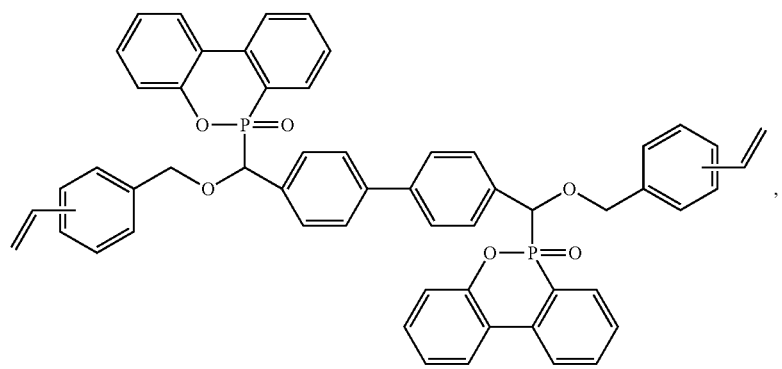
Formula (XXX)

-continued

Formula (XXXI)

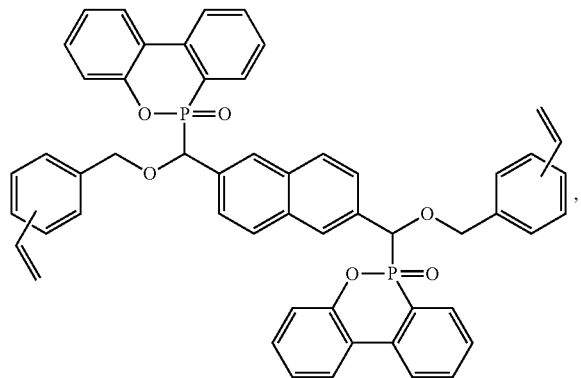

Formula (XXXII)

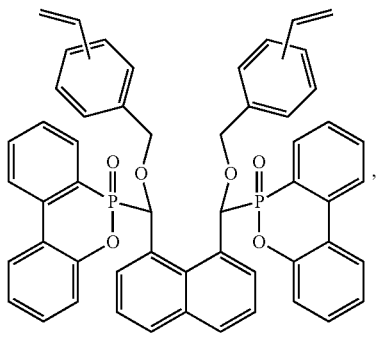

Formula (XXXIII)

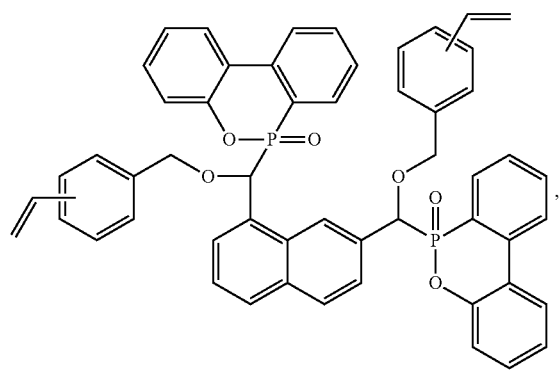

Formula (XXXIV)

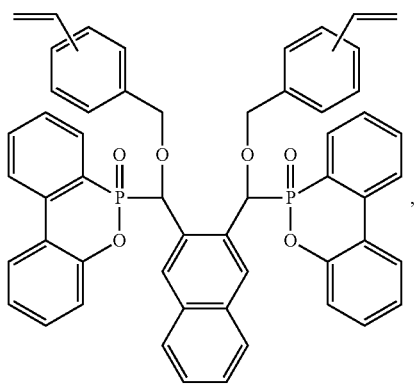

Formula (XXXV)

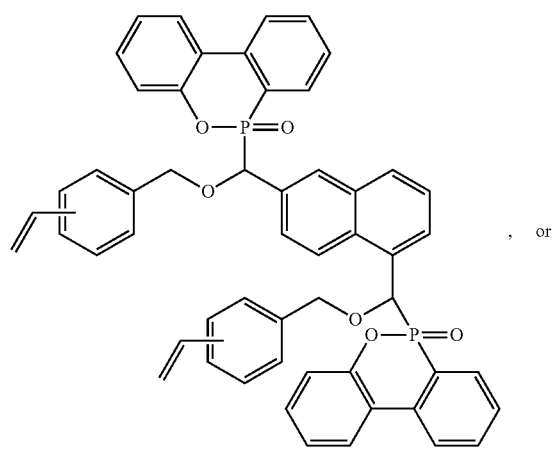

, or

Formula (XXXVI)

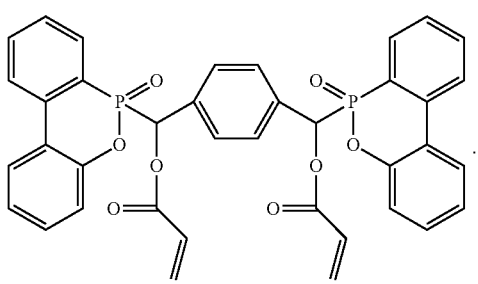

.

6. A resin composition comprising the phosphaphenanthrene-based compound according to claim 1.

7. The resin composition according to claim 6, wherein the resin composition comprises a reactant, an amount of the reactant is 100 parts by weight, an amount of the phosphaphenanthrene-based compound ranges from 5 parts by weight to 80 parts by weight, and the reactant comprises any one of epoxy resin, phenol resin, isocyanurate resin, cyanate ester resin, benzoxazine resin, styrene-maleic anhydride, polyester, maleimide, polyphenylene ether resin, amine curing agent, phenoxy resin, styrene, polyamide, polyimide, and polyolefin, or a combination thereof.

8. The resin composition according to claim 7, wherein the resin composition comprises an additive, and an amount of the reactant is 100 parts by weight, an amount of the additive is ranging from 0.01 parts by weight to 500 parts by weight, the additive comprises at least one component selected from a group consisting of a curing accelerator, a flame retardant, an inorganic filler, a solvent, a toughing agent, and a silane coupling agent.

9. A product comprising a cured product made from the resin composition according to claim 6.

10. A product comprising a semi-cured product made from the resin composition according to claim 6.

11. A method of manufacturing the phosphaphenanthrene-based compound of claim 1, comprising:

reacting 9,10-dihydro-9-oxa-10-phosphaphenanthrene-10-oxide with a di-aldehyde compound to form a phosphaphenanthrene-based compound having hydroxyl group; and reacting the phosphaphenanthrene-based compound having hydroxyl group with a vinyl compound to form the phosphaphenanthrene-based compound, the phosphaphenanthrene-based compound having the structure expressed by formula (I), wherein R and R' are each independently a hydrogen atom, a vinyl-substituted alkyl group with 3 to 20 carbon atoms, a vinyl-substituted cycloalkyl group with 8 to 20 carbon atoms, a vinyl-substituted benzyl group with 9 to 20 carbon atoms, a vinyl-substituted aromatic group with 8 to 20 carbon atoms, a vinyl- and carbonyl-substituted alkyl group with 4 to 20 carbon atoms, a vinyl- and carbonyl-substituted cycloalkyl group with 8 to 20 carbon atoms, a vinyl- and carbonyl-substituted aromatic group with 9 to 20 carbon atoms, a vinyl- and carbonyl-substituted benzyl group with 10 to 20 carbon atoms, or

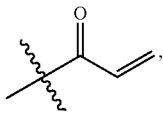 [SMILES: *C(=O)C=C]

wherein at least one of R or R' is not hydrogen; and
A is

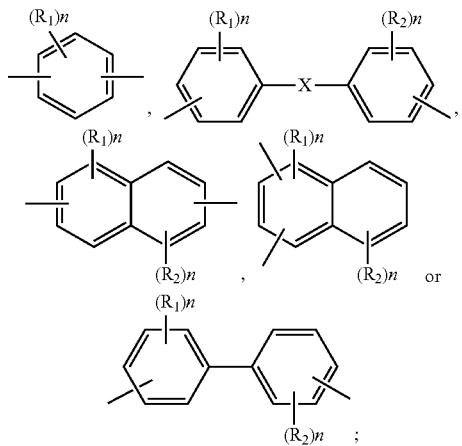

wherein $R_1$ and $R_2$ are each independently an alkyl group with 1 to 3 carbon atoms, X is —$CH_2$—,

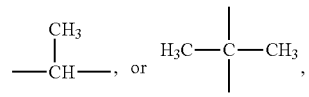

and n is an integer ranging from 0 to 4.

12. The method of manufacturing the phosphaphenanthrene-based compound according to claim 11, wherein the di-aldehyde compound is at least one selected from the group consisting of the following: 1,4-phthalaldehyde, 1,3-phthalaldehyde, 1,2-phthalaldehyde, 2,3-naphthalenedicarboxaldehyde, 1,6-naphthalenedicarboxaldehyde, 1,8-naphthalenedicarboxaldehyde, 1,7-naphthalenedicarboxaldehyde, 4,4'-biphenyldicarboxaldehyde, 4,4'-xenygloxal, bisphenol A based di-aldehyde, bisphenol F based di-aldehyde, and bisphenol E based di-aldehyde.

13. The method of manufacturing the phosphaphenanthrene-based compound according to claim 11, wherein the step of reacting the phosphaphenanthrene-based compound having hydroxyl group with the vinyl compound to form the phosphaphenanthrene-based compound comprises carrying out a reaction of the phosphaphenanthrene-based compound having hydroxyl group and the vinyl compound in the presence of hydroxide and tetrabutylammonium halide so as to form a vinyl-containing phosphaphenanthrene-based compound.

14. The method of manufacturing the phosphaphenanthrene-based compound according to claim 13, wherein an addition amount of the phosphaphenanthrene-based compound having hydroxyl group is 1 mole, an addition amount of the vinyl compound ranges from 2 moles to 4 moles, an addition amount of the hydroxide ranges from 2 moles to 4 moles, and an addition amount of the tetrabutylammonium halide ranges from 0.1 moles to 0.3 moles.

15. The method of manufacturing the phosphaphenanthrene-based compound according to claim 11, wherein a mole ratio of the 9,10-dihydro-9-oxa-10-phosphaphenanthrene-10-oxide and the di-aldehyde compound ranges from 2:1 to 4:1.

* * * * *